US010335045B2

(12) United States Patent
Sebe et al.

(10) Patent No.: US 10,335,045 B2
(45) Date of Patent: Jul. 2, 2019

(54) SELF-ADAPTIVE MATRIX COMPLETION FOR HEART RATE ESTIMATION FROM FACE VIDEOS UNDER REALISTIC CONDITIONS

(71) Applicants: Universita' degli Studi di Trento (University of Trento), Trento (IT); Fondazione Bruno Kessler (Bruno Kessler Foundation), Trento (IT); The Research Foundation for The State University of New York, Albany, NY (US); University of Pittsburgh—Of The Commonwealth of Higher Education, Pittsburgh, PA (US)

(72) Inventors: Niculae Sebe, Pergine Valsugana (IT); Xavier Alameda-Pineda, Trento (IT); Sergey Tulyakov, Trento (IT); Elisa Ricci, Trento (IT); Lijun Yin, Vestal, NY (US); Jeffrey F. Cohn, Pittsburgh, PA (US)

(73) Assignees: Universita degli Studi Di Trento, Trento (IT); Fondazione Bruno Kessler, Trento (IT); The Research Foundation for the State University of New York, Binghamton, NY (US); University of Pittsburgh of the Commonwealth of Higher Education, Pittsburgh, PA (US)

(*) Notice: Subject to any disclaimer, the term of this patent is extended or adjusted under 35 U.S.C. 154(b) by 0 days.

(21) Appl. No.: 15/631,346

(22) Filed: Jun. 23, 2017

(65) Prior Publication Data
US 2017/0367590 A1 Dec. 28, 2017

Related U.S. Application Data

(60) Provisional application No. 62/354,475, filed on Jun. 24, 2016.

(51) Int. Cl.
G06K 9/00 (2006.01)
A61B 5/024 (2006.01)
(Continued)

(52) U.S. Cl.
CPC ............ *A61B 5/024* (2013.01); *A61B 5/0077* (2013.01); *G06K 9/00268* (2013.01);
(Continued)

(58) Field of Classification Search
CPC ............ G06T 2207/30048; G06T 2207/10024
See application file for complete search history.

(56) References Cited

U.S. PATENT DOCUMENTS 4,509,528 A 4/1985 Sahota
5,672,875 A 9/1997 Block et al.
(Continued)

OTHER PUBLICATIONS

X. Alameda-Pineda, Y. Yan, E. Ricci, O. Lanz, and N. Sebe. Analyzing free-standing conversational groups: A multimodal approach. In ACM Multimedia, 2015.
(Continued)

*Primary Examiner* — Oneal R Mistry
(74) *Attorney, Agent, or Firm* — Tully Rinckey PLLC; Steven M. Hoffberg

(57) ABSTRACT

Recent studies in computer vision have shown that, while practically invisible to a human observer, skin color changes due to blood flow can be captured on face videos and, surprisingly, be used to estimate the heart rate (HR). While considerable progress has been made in the last few years, still many issues remain open. In particular, state-of-the-art approaches are not robust enough to operate in natural conditions (e.g. in case of spontaneous movements, facial expressions, or illumination changes). Opposite to previous approaches that estimate the HR by processing all the skin pixels inside a fixed region of interest, we introduce a
(Continued)

strategy to dynamically select face regions useful for robust HR estimation. The present approach, inspired by recent advances on matrix completion theory, allows us to predict the HR while simultaneously discover the best regions of the face to be used for estimation. Thorough experimental evaluation conducted on public benchmarks suggests that the proposed approach significantly outperforms state-of-the-art HR estimation methods in naturalistic conditions.

23 Claims, 5 Drawing Sheets

(51) Int. Cl.
| | |
|---|---|
| G06T 7/00 | (2017.01) |
| G06T 7/11 | (2017.01) |
| G06T 7/90 | (2017.01) |
| G06T 3/00 | (2006.01) |
| A61B 5/00 | (2006.01) |
| G06K 9/46 | (2006.01) |
| A61B 5/021 | (2006.01) |
| A61B 5/11 | (2006.01) |
| A61B 5/16 | (2006.01) |

(52) U.S. Cl.
CPC ..... *G06K 9/00281* (2013.01); *G06K 9/00315* (2013.01); *G06K 9/4652* (2013.01); *G06T 3/0093* (2013.01); *G06T 7/0016* (2013.01); *G06T 7/11* (2017.01); *G06T 7/90* (2017.01); *A61B 5/021* (2013.01); *A61B 5/1114* (2013.01); *A61B 5/165* (2013.01); *G06K 2009/00939* (2013.01); *G06T 2207/10016* (2013.01); *G06T 2207/10024* (2013.01); *G06T 2207/30048* (2013.01); *G06T 2207/30201* (2013.01)

(56) References Cited

U.S. PATENT DOCUMENTS

| | | | |
|---|---|---|---|
| 5,810,723 | A | 9/1998 | Aldrich |
| 6,064,065 | A | 5/2000 | Block et al. |
| 6,397,093 | B1 | 5/2002 | Aldrich |
| 6,420,709 | B1 | 7/2002 | Block et al. |
| 6,491,647 | B1 | 12/2002 | Bridger et al. |
| 6,513,532 | B2 | 2/2003 | Mault et al. |
| 6,644,976 | B2 | 11/2003 | Kullok et al. |
| 7,024,235 | B2 | 4/2006 | Melker et al. |
| 7,127,278 | B2 | 10/2006 | Melker et al. |
| 7,150,710 | B2 | 12/2006 | Haber et al. |
| 7,309,315 | B2 | 12/2007 | Kullok et al. |
| 7,351,327 | B2 | 4/2008 | Podrebarac et al. |
| 7,436,937 | B2 | 10/2008 | Clawson |
| 7,625,285 | B2 | 12/2009 | Breving |
| 7,654,901 | B2 | 2/2010 | Breving |
| 7,657,292 | B2 | 2/2010 | Baker, Jr. et al. |
| 7,878,965 | B2 | 2/2011 | Haber et al. |
| 7,887,502 | B2 | 2/2011 | Ross et al. |
| 7,918,779 | B2 | 4/2011 | Haber et al. |
| 8,135,448 | B2 | 3/2012 | Baker, Jr. et al. |
| 8,157,730 | B2 | 4/2012 | LeBoeuf et al. |
| 8,180,591 | B2 | 5/2012 | Yuen et al. |
| 8,180,592 | B2 | 5/2012 | Yuen et al. |
| 8,187,201 | B2 | 5/2012 | Lynn |
| 8,204,786 | B2 | 6/2012 | LeBoeuf et al. |
| 8,206,427 | B1 | 6/2012 | Ryan et al. |
| 8,277,384 | B2 | 10/2012 | Fine |
| 8,287,434 | B2 | 10/2012 | Zavadsky et al. |
| 8,311,769 | B2 | 11/2012 | Yuen et al. |
| 8,311,770 | B2 | 11/2012 | Yuen et al. |
| 8,317,854 | B1 | 11/2012 | Ryan et al. |
| 8,343,026 | B2 | 1/2013 | Gardiner et al. |
| 8,386,008 | B2 | 2/2013 | Yuen et al. |
| 8,437,980 | B2 | 5/2013 | Yuen et al. |
| 8,463,576 | B2 | 6/2013 | Yuen et al. |
| 8,463,577 | B2 | 6/2013 | Yuen et al. |
| 8,489,178 | B2 | 7/2013 | Wood et al. |
| 8,542,877 | B2 | 9/2013 | Jeanne et al. |
| 8,542,878 | B2 | 9/2013 | Cennini et al. |
| 8,543,185 | B2 | 9/2013 | Yuen et al. |
| 8,543,351 | B2 | 9/2013 | Yuen et al. |
| 8,548,770 | B2 | 10/2013 | Yuen et al. |
| 8,553,940 | B2 | 10/2013 | Kirenko et al. |
| 8,583,402 | B2 | 11/2013 | Yuen et al. |
| 8,585,607 | B2 | 11/2013 | Klap et al. |
| 8,606,344 | B2 | 12/2013 | DiMaio et al. |
| 8,617,081 | B2 | 12/2013 | Mestha et al. |
| 8,634,591 | B2 | 1/2014 | Jeanne et al. |
| 8,649,562 | B2 | 2/2014 | De Haan et al. |
| 8,666,116 | B2 | 3/2014 | Kirenko et al. |
| 8,670,953 | B2 | 3/2014 | Yuen et al. |
| 8,702,607 | B2 | 4/2014 | LeBoeuf et al. |
| 8,718,447 | B2 | 5/2014 | Yang et al. |
| 8,718,748 | B2 | 5/2014 | Reinhold |
| 8,725,311 | B1 | 5/2014 | Breed |
| 8,728,001 | B2 | 5/2014 | Lynn |
| 8,734,360 | B2 | 5/2014 | Klap et al. |
| 8,751,194 | B2 | 6/2014 | Panther et al. |
| 8,755,857 | B2 | 6/2014 | Melker et al. |
| 8,768,438 | B2 | 7/2014 | Mestha et al. |
| 8,768,648 | B2 | 7/2014 | Panther et al. |
| 8,781,791 | B2 | 7/2014 | Panther et al. |
| 8,792,969 | B2 | 7/2014 | Bernal et al. |
| 8,801,620 | B2 | 8/2014 | Melker et al. |
| 8,805,019 | B2 | 8/2014 | Jeanne et al. |
| 8,818,041 | B2 | 8/2014 | Cennini et al. |
| 8,821,418 | B2 | 9/2014 | Meger et al. |
| 8,838,209 | B2 | 9/2014 | Mestha et al. |
| 8,849,610 | B2 | 9/2014 | Molettiere et al. |
| 8,855,384 | B2 | 10/2014 | Kyal et al. |
| 8,862,196 | B2 | 10/2014 | Lynn |
| 8,868,149 | B2 | 10/2014 | Eisen et al. |
| 8,868,377 | B2 | 10/2014 | Yuen et al. |
| 8,920,332 | B2 | 12/2014 | Hong et al. |
| 8,932,227 | B2 | 1/2015 | Lynn |
| 8,935,119 | B2 | 1/2015 | Yuen |
| 8,938,097 | B2 | 1/2015 | Kirenko et al. |
| 8,945,017 | B2 | 2/2015 | Venkatraman et al. |
| 8,948,832 | B2 | 2/2015 | Hong et al. |
| 8,954,135 | B2 | 2/2015 | Yuen et al. |
| 8,954,290 | B2 | 2/2015 | Yuen et al. |
| 8,956,303 | B2 | 2/2015 | Hong et al. |
| 8,961,185 | B2 | 2/2015 | Bleich et al. |
| 8,961,415 | B2 | 2/2015 | LeBoeuf et al. |
| 8,961,932 | B2 | 2/2015 | Silverman |
| 8,965,730 | B2 | 2/2015 | Yuen |
| 8,977,347 | B2 | 3/2015 | Mestha et al. |
| 8,984,622 | B1 | 3/2015 | Baldwin et al. |
| 8,998,815 | B2 | 4/2015 | Venkatraman et al. |
| 9,002,458 | B2 | 4/2015 | Pal et al. |
| 9,005,129 | B2 | 4/2015 | Venkatraman et al. |
| 9,011,316 | B2 | 4/2015 | Mertens et al. |
| 9,014,790 | B2 | 4/2015 | Richards et al. |
| 9,014,811 | B2 | 4/2015 | Pal et al. |
| 9,020,185 | B2 | 4/2015 | Mestha et al. |
| 9,025,826 | B2 | 5/2015 | Kirenko et al. |
| 9,036,877 | B2 | 5/2015 | Kyal et al. |
| 9,042,952 | B2 | 5/2015 | Lynn et al. |
| 9,044,149 | B2 | 6/2015 | Richards et al. |
| 9,044,171 | B2 | 6/2015 | Venkatraman et al. |
| 9,053,222 | B2 | 6/2015 | Lynn et al. |
| 9,075,906 | B2 | 7/2015 | Hyde et al. |
| 9,079,060 | B2 | 7/2015 | Hong et al. |
| 9,098,901 | B2 | 8/2015 | Shan et al. |
| 9,113,794 | B2 | 8/2015 | Hong et al. |
| 9,113,795 | B2 | 8/2015 | Hong et al. |
| 9,113,823 | B2 | 8/2015 | Yuen et al. |
| 9,125,606 | B2 | 9/2015 | Verkruijsse et al. |
| 9,149,216 | B2 | 10/2015 | Eisen et al. |
| 9,155,826 | B2 | 10/2015 | Ross et al. |
| 9,167,991 | B2 | 10/2015 | Yuen et al. |

(56) References Cited

U.S. PATENT DOCUMENTS

| | | |
|---|---|---|
| 9,168,419 B2 | 10/2015 | Hong et al. |
| 9,198,586 B2 | 12/2015 | Melker |
| 9,198,604 B2 | 12/2015 | Venkatraman et al. |
| 9,232,915 B2 | 1/2016 | Chua et al. |
| 9,233,244 B2 | 1/2016 | Pal et al. |
| 9,237,855 B2 | 1/2016 | Hong et al. |
| 9,241,635 B2 | 1/2016 | Yuen et al. |
| 9,241,674 B2 | 1/2016 | Van Leest |
| 9,265,456 B2 | 2/2016 | Kirenko et al. |
| 9,282,902 B2 | 3/2016 | Richards et al. |
| 9,301,710 B2 | 4/2016 | Mestha et al. |
| 9,307,917 B2 | 4/2016 | Hong et al. |
| 9,333,351 B2 | 5/2016 | Arnold et al. |
| 9,336,594 B2 | 5/2016 | Kyal et al. |
| 9,345,427 B2 | 5/2016 | Wood et al. |
| 9,351,649 B2 | 5/2016 | Mestha et al. |
| 9,357,955 B2 | 6/2016 | Lu et al. |
| 9,364,157 B2 | 6/2016 | Lu et al. |
| 9,370,634 B2 | 6/2016 | Melker et al. |
| 9,374,279 B2 | 6/2016 | Yuen et al. |
| 9,385,768 B2 | 7/2016 | De Haan |
| 9,402,552 B2 | 8/2016 | Richards et al. |
| 9,410,979 B2 | 8/2016 | Yuen et al. |
| 9,443,304 B2 | 9/2016 | Damkat |
| 9,444,998 B2 | 9/2016 | Kim et al. |
| 9,451,905 B2 | 9/2016 | Op Den Buijs et al. |
| 9,456,787 B2 | 10/2016 | Venkatraman et al. |
| 9,468,378 B2 | 10/2016 | Lynn et al. |
| 9,472,033 B2 | 10/2016 | Agrafioti et al. |
| 9,480,434 B2 | 11/2016 | De Haan et al. |
| 9,483,837 B2 | 11/2016 | Xu et al. |
| 9,495,008 B2 | 11/2016 | Savastinuk et al. |
| 9,498,137 B2 | 11/2016 | Kovacs |
| 9,503,142 B2 | 11/2016 | Sakong et al. |
| 9,504,408 B2 | 11/2016 | Hong et al. |
| 9,504,426 B2 | 11/2016 | Kyal et al. |
| 9,510,758 B2 | 12/2016 | Warger, II et al. |
| 9,520,638 B2 | 12/2016 | Baringer et al. |
| 9,521,962 B2 | 12/2016 | LeBoeuf |
| 9,522,317 B2 | 12/2016 | Bleich et al. |
| 9,524,548 B2 | 12/2016 | Kirenko et al. |
| 9,538,921 B2 | 1/2017 | LeBoeuf et al. |
| 9,543,636 B2 | 1/2017 | Baringer et al. |
| 9,546,898 B2 | 1/2017 | Kovacs |
| 9,568,354 B2 | 2/2017 | Kovacs et al. |
| 9,568,492 B2 | 2/2017 | Yuen |
| 9,569,979 B2 | 2/2017 | Masaoka |
| 9,572,533 B2 | 2/2017 | Venkatraman et al. |
| 9,582,035 B2 | 2/2017 | Connor |
| 9,582,879 B2 | 2/2017 | Cheng et al. |
| 9,596,990 B2 | 3/2017 | Park et al. |
| 9,597,014 B2 | 3/2017 | Venkatraman et al. |
| 9,599,632 B2 | 3/2017 | Yuen |
| 9,603,524 B2 | 3/2017 | Park et al. |
| 9,607,138 B1 | 3/2017 | Baldwin et al. |
| 9,615,749 B2 | 4/2017 | Clifton et al. |
| 9,620,914 B2 | 4/2017 | Park et al. |
| 9,639,170 B2 | 5/2017 | Yuen et al. |
| 9,641,239 B2 | 5/2017 | Panther et al. |
| 9,642,536 B2 | 5/2017 | Kashef et al. |
| 9,655,548 B2 | 5/2017 | Hong et al. |
| 9,659,229 B2 | 5/2017 | Clifton et al. |
| 9,662,053 B2 | 5/2017 | Richards et al. |
| 9,665,784 B2 | 5/2017 | Derakhshani et al. |
| 9,668,661 B2 | 6/2017 | Melker et al. |
| 9,675,281 B2 | 6/2017 | Arnold et al. |
| 9,675,291 B2 | 6/2017 | Braspenning et al. |
| 9,682,711 B2 | 6/2017 | Lee |
| 9,693,696 B2 | 7/2017 | Kovacs et al. |
| 9,697,414 B2 | 7/2017 | Baldwin et al. |
| 9,697,599 B2 | 7/2017 | Prasad et al. |
| 9,707,466 B2 | 7/2017 | Bleich et al. |
| 9,717,417 B2 | 8/2017 | DiMaio et al. |
| 9,717,836 B2 | 8/2017 | Melker |
| 9,729,693 B1 | 8/2017 | Munaretto |
| 9,750,977 B2 | 9/2017 | Yuen et al. |
| 9,753,543 B2 | 9/2017 | Jeon et al. |
| 9,767,358 B2 | 9/2017 | Xue et al. |
| 9,770,213 B2 | 9/2017 | Kirenko et al. |
| 9,782,132 B2 | 10/2017 | Golda et al. |
| 9,788,785 B2 | 10/2017 | LeBoeuf |
| 9,794,474 B2 | 10/2017 | Kim et al. |
| 9,794,653 B2 | 10/2017 | Aumer et al. |
| 9,801,547 B2 | 10/2017 | Yuen et al. |
| 9,801,552 B2 | 10/2017 | Romesburg |
| 9,808,185 B2 | 11/2017 | Arnold et al. |
| 9,814,423 B2 | 11/2017 | Jain et al. |
| 9,838,645 B2 | 12/2017 | Hyde et al. |
| 9,839,375 B2 | 12/2017 | Shan et al. |
| 9,842,392 B2 | 12/2017 | De Haan |
| 9,846,763 B2 | 12/2017 | Hyde et al. |
| 9,852,507 B2 | 12/2017 | Gunther et al. |
| 9,861,126 B2 | 1/2018 | Utley et al. |
| 9,867,513 B1 | 1/2018 | Hall et al. |
| 9,869,973 B2 | 1/2018 | Raymann et al. |
| 9,883,365 B2 | 1/2018 | Kwon et al. |
| 9,886,034 B2 | 2/2018 | Boesch et al. |
| 9,901,306 B2 | 2/2018 | Adams et al. |
| 9,924,896 B2 | 3/2018 | De Haan et al. |
| 9,928,607 B2 | 3/2018 | Jeanne et al. |
| 9,936,880 B2 | 4/2018 | Kumar et al. |
| 9,943,266 B2 | 4/2018 | Adams et al. |
| 9,956,470 B2 | 5/2018 | Bleich et al. |
| 9,962,090 B2 | 5/2018 | DiMaio et al. |
| 9,962,095 B2 | 5/2018 | Ahmad et al. |
| 9,971,314 B2 | 5/2018 | Lee et al. |
| 9,974,479 B2 | 5/2018 | Melker |
| 9,980,658 B2 | 5/2018 | Wang et al. |
| 9,983,670 B2 | 5/2018 | Coleman et al. |
| 9,987,489 B2 | 6/2018 | Goodall et al. |
| 9,993,204 B2 | 6/2018 | Romesburg |
| 9,996,917 B2 | 6/2018 | Jeanne et al. |
| 9,999,355 B2 | 6/2018 | Kirenko |
| 2001/0049470 A1 | 12/2001 | Mault et al. |
| 2003/0065257 A1 | 4/2003 | Mault et al. |
| 2003/0068605 A1 | 4/2003 | Kullok et al. |
| 2003/0130709 A1 | 7/2003 | D.C. et al. |
| 2003/0195040 A1 | 10/2003 | Breving |
| 2004/0049124 A1 | 3/2004 | Kullok et al. |
| 2004/0072133 A1 | 4/2004 | Kullok et al. |
| 2004/0229692 A1 | 11/2004 | Breving |
| 2004/0230108 A1 | 11/2004 | Melker et al. |
| 2004/0260161 A1 | 12/2004 | Melker et al. |
| 2006/0009700 A1 | 1/2006 | Brumfield et al. |
| 2006/0111620 A1 | 5/2006 | Squilla et al. |
| 2006/0253016 A1 | 11/2006 | Baker et al. |
| 2006/0258896 A1 | 11/2006 | Haber et al. |
| 2006/0293921 A1 | 12/2006 | McCarthy et al. |
| 2007/0027375 A1 | 2/2007 | Melker et al. |
| 2007/0073113 A1 | 3/2007 | Squilla et al. |
| 2007/0088833 A1 | 4/2007 | Yang et al. |
| 2007/0116189 A1 | 5/2007 | Clawson |
| 2007/0118027 A1 | 5/2007 | Baker et al. |
| 2007/0207858 A1 | 9/2007 | Breving |
| 2007/0225606 A1 | 9/2007 | Naghavi et al. |
| 2007/0225614 A1 | 9/2007 | Naghavi et al. |
| 2008/0027330 A1 | 1/2008 | Naghavi et al. |
| 2008/0045818 A1 | 2/2008 | Wood et al. |
| 2008/0051858 A1 | 2/2008 | Haber et al. |
| 2008/0067132 A1 | 3/2008 | Ross et al. |
| 2008/0146892 A1 | 6/2008 | LeBoeuf et al. |
| 2008/0190430 A1 | 8/2008 | Melker et al. |
| 2008/0241199 A1 | 10/2008 | Silverman |
| 2009/0143655 A1 | 6/2009 | Shani |
| 2009/0182204 A1 | 7/2009 | Semler et al. |
| 2009/0203998 A1 | 8/2009 | Klinghult et al. |
| 2009/0209834 A1 | 8/2009 | Fine |
| 2009/0226071 A1 | 9/2009 | Schuler et al. |
| 2010/0081941 A1 | 4/2010 | Naghavi et al. |
| 2010/0217099 A1 | 8/2010 | LeBoeuf et al. |
| 2011/0046498 A1 | 2/2011 | Klap et al. |
| 2011/0059422 A1 | 3/2011 | Masaoka |
| 2011/0082355 A1 | 4/2011 | Eisen et al. |
| 2011/0098112 A1 | 4/2011 | LeBoeuf et al. |

(56) References Cited

U.S. PATENT DOCUMENTS

| | | |
|---|---|---|
| 2011/0098545 A1 | 4/2011 | Ross et al. |
| 2011/0106627 A1 | 5/2011 | LeBoeuf et al. |
| 2011/0112442 A1 | 5/2011 | Meger et al. |
| 2011/0178581 A1 | 7/2011 | Haber et al. |
| 2011/0251021 A1 | 10/2011 | Zavadsky et al. |
| 2011/0251493 A1 | 10/2011 | Poh et al. |
| 2011/0270050 A1 | 11/2011 | Naghavi et al. |
| 2011/0282169 A1 | 11/2011 | Grudic et al. |
| 2011/0311119 A1 | 12/2011 | Jeanne et al. |
| 2011/0311143 A1 | 12/2011 | Cennini et al. |
| 2011/0319724 A1 | 12/2011 | Cox |
| 2012/0022338 A1 | 1/2012 | Subramaniam et al. |
| 2012/0053469 A1 | 3/2012 | Melker |
| 2012/0065514 A1 | 3/2012 | Naghavi et al. |
| 2012/0078069 A1 | 3/2012 | Melker |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0127351 A1 | 5/2012 | Vlutters et al. |
| 2012/0141000 A1 | 6/2012 | Jeanne et al. |
| 2012/0195469 A1 | 8/2012 | Kirenko et al. |
| 2012/0195473 A1 | 8/2012 | De Haan et al. |
| 2012/0195486 A1 | 8/2012 | Kirenko et al. |
| 2012/0197137 A1 | 8/2012 | Jeanne et al. |
| 2012/0197737 A1 | 8/2012 | LeBoeuf et al. |
| 2012/0203081 A1 | 8/2012 | LeBoeuf et al. |
| 2012/0226111 A1 | 9/2012 | LeBoeuf et al. |
| 2012/0226112 A1 | 9/2012 | LeBoeuf et al. |
| 2012/0226334 A1 | 9/2012 | Gardiner et al. |
| 2012/0226471 A1 | 9/2012 | Yuen et al. |
| 2012/0226472 A1 | 9/2012 | Yuen et al. |
| 2012/0253201 A1 | 10/2012 | Reinhold |
| 2012/0265296 A1 | 10/2012 | McNamara et al. |
| 2012/0308971 A1 | 12/2012 | Shin et al. |
| 2013/0065680 A1 | 3/2013 | Zavadsky et al. |
| 2013/0073254 A1 | 3/2013 | Yuen et al. |
| 2013/0073255 A1 | 3/2013 | Yuen et al. |
| 2013/0077823 A1* | 3/2013 | Mestha ............... A61B 5/0075 382/103 |
| 2013/0079649 A1 | 3/2013 | Mestha et al. |
| 2013/0080113 A1 | 3/2013 | Yuen et al. |
| 2013/0096843 A1 | 4/2013 | Yuen et al. |
| 2013/0116503 A1 | 5/2013 | Mertens et al. |
| 2013/0131475 A1 | 5/2013 | Eisen et al. |
| 2013/0151196 A1 | 6/2013 | Yuen et al. |
| 2013/0158369 A1 | 6/2013 | Yuen et al. |
| 2013/0171599 A1 | 7/2013 | Bleich et al. |
| 2013/0197401 A1 | 8/2013 | Sato et al. |
| 2013/0225950 A1 | 8/2013 | Van Elswijk et al. |
| 2013/0268236 A1 | 10/2013 | Yuen et al. |
| 2013/0272393 A1 | 10/2013 | Kirenko et al. |
| 2013/0276785 A1 | 10/2013 | Melker et al. |
| 2013/0281795 A1 | 10/2013 | Varadan |
| 2013/0281815 A1 | 10/2013 | Varadan |
| 2013/0282040 A1 | 10/2013 | Jun |
| 2013/0283162 A1 | 10/2013 | Aronsson et al. |
| 2013/0289366 A1 | 10/2013 | Chua et al. |
| 2013/0294505 A1 | 11/2013 | Kirenko et al. |
| 2013/0296660 A1* | 11/2013 | Tsien ............... A61B 5/0077 600/301 |
| 2013/0297220 A1 | 11/2013 | Yuen et al. |
| 2013/0310656 A1 | 11/2013 | Lim et al. |
| 2013/0345568 A1 | 12/2013 | Mestha et al. |
| 2013/0345569 A1 | 12/2013 | Mestha et al. |
| 2014/0023235 A1 | 1/2014 | Cennini et al. |
| 2014/0023236 A1 | 1/2014 | Jeanne et al. |
| 2014/0024952 A1 | 1/2014 | Wood et al. |
| 2014/0028546 A1 | 1/2014 | Jeon et al. |
| 2014/0031696 A1 | 1/2014 | Schmeitz et al. |
| 2014/0037163 A1 | 2/2014 | Kirenko et al. |
| 2014/0046209 A1 | 2/2014 | Klap et al. |
| 2014/0051941 A1 | 2/2014 | Messerschmidt |
| 2014/0058217 A1 | 2/2014 | Giovangrandi |
| 2014/0067278 A1 | 3/2014 | Yuen et al. |
| 2014/0086462 A1 | 3/2014 | Shan et al. |
| 2014/0094666 A1 | 4/2014 | Fine |
| 2014/0094670 A1 | 4/2014 | Melker et al. |
| 2014/0104405 A1 | 4/2014 | Weidl et al. |
| 2014/0107493 A1 | 4/2014 | Yuen et al. |
| 2014/0114580 A1 | 4/2014 | Chen et al. |
| 2014/0121471 A1 | 5/2014 | Walker |
| 2014/0125491 A1 | 5/2014 | Park et al. |
| 2014/0125618 A1 | 5/2014 | Panther et al. |
| 2014/0125619 A1 | 5/2014 | Panther et al. |
| 2014/0125620 A1 | 5/2014 | Panther et al. |
| 2014/0127996 A1 | 5/2014 | Park et al. |
| 2014/0135598 A1 | 5/2014 | Weidl et al. |
| 2014/0135612 A1 | 5/2014 | Yuen et al. |
| 2014/0139656 A1 | 5/2014 | Jeanne et al. |
| 2014/0148663 A1 | 5/2014 | Bresch et al. |
| 2014/0153800 A1 | 6/2014 | Kirenko et al. |
| 2014/0155704 A1 | 6/2014 | Melker et al. |
| 2014/0155713 A1 | 6/2014 | Melker et al. |
| 2014/0155759 A1 | 6/2014 | Kaestle et al. |
| 2014/0158132 A1 | 6/2014 | Melker |
| 2014/0164014 A1 | 6/2014 | Kim et al. |
| 2014/0180026 A1 | 6/2014 | Melker et al. |
| 2014/0180132 A1 | 6/2014 | Shan et al. |
| 2014/0192177 A1 | 7/2014 | Bartula et al. |
| 2014/0200460 A1 | 7/2014 | Johnson et al. |
| 2014/0206954 A1 | 7/2014 | Yuen et al. |
| 2014/0206965 A1 | 7/2014 | De Haan et al. |
| 2014/0207292 A1 | 7/2014 | Ramagem et al. |
| 2014/0213861 A1 | 7/2014 | Van Leest |
| 2014/0218496 A1 | 8/2014 | Park et al. |
| 2014/0221781 A1 | 8/2014 | Schrauf et al. |
| 2014/0221845 A1 | 8/2014 | Mestha et al. |
| 2014/0221847 A1 | 8/2014 | Dubielczyk et al. |
| 2014/0221866 A1 | 8/2014 | Quy |
| 2014/0228649 A1 | 8/2014 | Rayner et al. |
| 2014/0234815 A1 | 8/2014 | Jang et al. |
| 2014/0243648 A1 | 8/2014 | Dubielczyk |
| 2014/0253709 A1 | 9/2014 | Bresch et al. |
| 2014/0266939 A1 | 9/2014 | Baringer et al. |
| 2014/0273858 A1 | 9/2014 | Panther et al. |
| 2014/0275832 A1 | 9/2014 | Muehlsteff et al. |
| 2014/0275850 A1 | 9/2014 | Venkatraman et al. |
| 2014/0275852 A1 | 9/2014 | Hong et al. |
| 2014/0275854 A1 | 9/2014 | Venkatraman et al. |
| 2014/0275855 A1 | 9/2014 | LeBoeuf et al. |
| 2014/0275880 A1 | 9/2014 | Verkruijsse et al. |
| 2014/0276089 A1 | 9/2014 | Kirenko et al. |
| 2014/0276090 A1 | 9/2014 | Breed |
| 2014/0276099 A1 | 9/2014 | Kirenko et al. |
| 2014/0276104 A1 | 9/2014 | Tao et al. |
| 2014/0276118 A1 | 9/2014 | Tsouri et al. |
| 2014/0276119 A1 | 9/2014 | Venkatraman et al. |
| 2014/0278220 A1 | 9/2014 | Yuen |
| 2014/0278229 A1 | 9/2014 | Hong et al. |
| 2014/0287833 A1 | 9/2014 | LeBoeuf et al. |
| 2014/0288390 A1 | 9/2014 | Hong et al. |
| 2014/0288391 A1 | 9/2014 | Hong et al. |
| 2014/0288392 A1 | 9/2014 | Hong et al. |
| 2014/0288396 A1 | 9/2014 | LeBoeuf et al. |
| 2014/0288435 A1 | 9/2014 | Richards et al. |
| 2014/0288436 A1 | 9/2014 | Venkatraman et al. |
| 2014/0288438 A1 | 9/2014 | Venkatraman et al. |
| 2014/0297217 A1 | 10/2014 | Yuen |
| 2014/0297218 A1 | 10/2014 | Yuen |
| 2014/0303454 A1 | 10/2014 | Clifton et al. |
| 2014/0305204 A1 | 10/2014 | Hong et al. |
| 2014/0316305 A1 | 10/2014 | Venkatraman et al. |
| 2014/0323888 A1 | 10/2014 | Kyal et al. |
| 2014/0343349 A1 | 11/2014 | Borsody |
| 2014/0343867 A1 | 11/2014 | Yuen et al. |
| 2014/0358012 A1 | 12/2014 | Richards et al. |
| 2014/0358017 A1 | 12/2014 | Op Den Buijs et al. |
| 2014/0371583 A1 | 12/2014 | Flower |
| 2015/0005646 A1* | 1/2015 | Balakrishnan ......... A61B 5/024 600/479 |
| 2015/0005680 A1 | 1/2015 | Lipani |

(56) References Cited

U.S. PATENT DOCUMENTS

| | | |
|---|---|---|
| 2015/0005840 A1 | 1/2015 | Pal et al. |
| 2015/0005841 A1 | 1/2015 | Pal et al. |
| 2015/0011898 A1 | 1/2015 | Romesburg |
| 2015/0025334 A1 | 1/2015 | Jain |
| 2015/0025335 A1 | 1/2015 | Jain et al. |
| 2015/0025393 A1 | 1/2015 | Hong et al. |
| 2015/0025394 A1 | 1/2015 | Hong et al. |
| 2015/0031965 A1 | 1/2015 | Visvanathan et al. |
| 2015/0051521 A1 | 2/2015 | Woerlee et al. |
| 2015/0057511 A1 | 2/2015 | Basu |
| 2015/0080746 A1 | 3/2015 | Bleich et al. |
| 2015/0085136 A1 | 3/2015 | Bernal et al. |
| 2015/0094552 A1 | 4/2015 | Golda et al. |
| 2015/0101609 A1 | 4/2015 | Melker et al. |
| 2015/0104088 A1 | 4/2015 | Kirenko et al. |
| 2015/0105638 A1 | 4/2015 | Eisen et al. |
| 2015/0119654 A1 | 4/2015 | Martin et al. |
| 2015/0119725 A1 | 4/2015 | Martin et al. |
| 2015/0122018 A1 | 5/2015 | Yuen |
| 2015/0125051 A1 | 5/2015 | Damkat |
| 2015/0126824 A1 | 5/2015 | LeBoeuf et al. |
| 2015/0126888 A1 | 5/2015 | Patel et al. |
| 2015/0134268 A1 | 5/2015 | Yuen et al. |
| 2015/0141772 A1 | 5/2015 | LeBoeuf et al. |
| 2015/0145673 A1 | 5/2015 | Choi et al. |
| 2015/0148622 A1 | 5/2015 | Moyer et al. |
| 2015/0148637 A1 | 5/2015 | Golda et al. |
| 2015/0148687 A1 | 5/2015 | Kitajima et al. |
| 2015/0148691 A1 | 5/2015 | Moyer et al. |
| 2015/0164349 A1 | 6/2015 | Gopalakrishnan et al. |
| 2015/0165200 A1 | 6/2015 | Arnold et al. |
| 2015/0173631 A1 | 6/2015 | Richards et al. |
| 2015/0174403 A1 | 6/2015 | Pal et al. |
| 2015/0182132 A1 | 7/2015 | Harris et al. |
| 2015/0182137 A1 | 7/2015 | Flower et al. |
| 2015/0186711 A1 | 7/2015 | Baldwin et al. |
| 2015/0190062 A1 | 7/2015 | Han et al. |
| 2015/0190077 A1 | 7/2015 | Kim et al. |
| 2015/0190090 A1 | 7/2015 | Silverman |
| 2015/0192438 A1 | 7/2015 | Choi et al. |
| 2015/0196256 A1 | 7/2015 | Venkatraman et al. |
| 2015/0196455 A1 | 7/2015 | Mertens et al. |
| 2015/0199010 A1 | 7/2015 | Coleman et al. |
| 2015/0201853 A1 | 7/2015 | Hong et al. |
| 2015/0201854 A1 | 7/2015 | Hong et al. |
| 2015/0208923 A1 | 7/2015 | Akl et al. |
| 2015/0208950 A1 | 7/2015 | Akl et al. |
| 2015/0216425 A1 | 8/2015 | Gladshtein et al. |
| 2015/0223698 A1 | 8/2015 | Subramaniam et al. |
| 2015/0223700 A1 | 8/2015 | Kirenko |
| 2015/0223708 A1 | 8/2015 | Richards et al. |
| 2015/0229341 A1 | 8/2015 | Fung et al. |
| 2015/0230735 A1 | 8/2015 | Venkatraman et al. |
| 2015/0236740 A1 | 8/2015 | De Haan |
| 2015/0238120 A1 | 8/2015 | Shan et al. |
| 2015/0241936 A1 | 8/2015 | Hur et al. |
| 2015/0242608 A1 | 8/2015 | Kim et al. |
| 2015/0245186 A1 | 8/2015 | Park et al. |
| 2015/0250391 A1 | 9/2015 | Kyal et al. |
| 2015/0257653 A1 | 9/2015 | Hyde et al. |
| 2015/0257659 A1 | 9/2015 | Broers et al. |
| 2015/0259110 A1 | 9/2015 | Blackburn |
| 2015/0263774 A1 | 9/2015 | Sa et al. |
| 2015/0264028 A1 | 9/2015 | Kim et al. |
| 2015/0264045 A1 | 9/2015 | Blondeau |
| 2015/0265161 A1 | 9/2015 | Hernandez et al. |
| 2015/0265164 A1 | 9/2015 | Gopalakrishnan et al. |
| 2015/0265212 A1 | 9/2015 | Bruekers et al. |
| 2015/0272452 A1 | 10/2015 | Mullin et al. |
| 2015/0272489 A1 | 10/2015 | Kirenko et al. |
| 2015/0272494 A1 | 10/2015 | Fuerst |
| 2015/0280181 A1 | 10/2015 | Kim et al. |
| 2015/0280357 A1 | 10/2015 | Park et al. |
| 2015/0282724 A1 | 10/2015 | McDuff et al. |
| 2015/0282769 A1 | 10/2015 | Song et al. |
| 2015/0293115 A1 | 10/2015 | Buhimschi et al. |
| 2015/0293592 A1 | 10/2015 | Cheong et al. |
| 2015/0297142 A1 | 10/2015 | De Jaam |
| 2015/0302158 A1 | 10/2015 | Morris et al. |
| 2015/0309535 A1 | 10/2015 | Connor |
| 2015/0314166 A1 | 11/2015 | Hong et al. |
| 2015/0317120 A1 | 11/2015 | Kim et al. |
| 2015/0320363 A1 | 11/2015 | De Haan |
| 2015/0351699 A1 | 12/2015 | Addison et al. |
| 2015/0366455 A1 | 12/2015 | Bezemer |
| 2015/0366492 A1 | 12/2015 | De Haan et al. |
| 2015/0366504 A1 | 12/2015 | Connor |
| 2015/0366518 A1 | 12/2015 | Sampson |
| 2015/0370320 A1 | 12/2015 | Connor |
| 2015/0374249 A1 | 12/2015 | Elliott et al. |
| 2015/0378433 A1 | 12/2015 | Savastinuk et al. |
| 2015/0379238 A1 | 12/2015 | Connor |
| 2015/0379362 A1 | 12/2015 | Calmes et al. |
| 2015/0379370 A1 | 12/2015 | Clifton et al. |
| 2016/0007934 A1 | 1/2016 | Arnold et al. |
| 2016/0008632 A1 | 1/2016 | Wetmore et al. |
| 2016/0015308 A1 | 1/2016 | Kirenko et al. |
| 2016/0022175 A1 | 1/2016 | Arnold et al. |
| 2016/0022201 A1 | 1/2016 | Arnold et al. |
| 2016/0022203 A1 | 1/2016 | Arnold et al. |
| 2016/0022220 A1 | 1/2016 | Lee et al. |
| 2016/0023666 A1 | 1/2016 | Lee |
| 2016/0029898 A1 | 2/2016 | LeBoeuf et al. |
| 2016/0029964 A1 | 2/2016 | LeBoeuf et al. |
| 2016/0029973 A1 | 2/2016 | Kahlman |
| 2016/0036118 A1 | 2/2016 | Baringer et al. |
| 2016/0051169 A1 | 2/2016 | Hong et al. |
| 2016/0055635 A1 | 2/2016 | Yu et al. |
| 2016/0058367 A1 | 3/2016 | Raghuram et al. |
| 2016/0058375 A1 | 3/2016 | Rothkopf |
| 2016/0058376 A1 | 3/2016 | Baek et al. |
| 2016/0062321 A1 | 3/2016 | Lee et al. |
| 2016/0065840 A1 | 3/2016 | Kim et al. |
| 2016/0066844 A1 | 3/2016 | Venkatraman et al. |
| 2016/0067494 A1 | 3/2016 | Lipani |
| 2016/0074276 A1 | 3/2016 | Scheuring et al. |
| 2016/0074661 A1 | 3/2016 | Lipani |
| 2016/0084869 A1 | 3/2016 | Yuen et al. |
| 2016/0089033 A1 | 3/2016 | Saponas et al. |
| 2016/0089041 A1* | 3/2016 | Keat .......... A61B 5/72 600/479 |
| 2016/0094899 A1 | 3/2016 | Aumer et al. |
| 2016/0095524 A1 | 4/2016 | Estepp et al. |
| 2016/0095731 A1 | 4/2016 | Connor |
| 2016/0100765 A1 | 4/2016 | Muehlsteff et al. |
| 2016/0100805 A1 | 4/2016 | Muehlsteff et al. |
| 2016/0106360 A1 | 4/2016 | Choi et al. |
| 2016/0106365 A1 | 4/2016 | Choi et al. |
| 2016/0106371 A1 | 4/2016 | Lee et al. |
| 2016/0110868 A1 | 4/2016 | Cheng et al. |
| 2016/0113526 A1 | 4/2016 | Nageshwar et al. |
| 2016/0113531 A1 | 4/2016 | Visvanathan et al. |
| 2016/0117544 A1 | 4/2016 | Hoyos et al. |
| 2016/0117937 A1 | 4/2016 | Penders et al. |
| 2016/0120482 A1 | 5/2016 | Kirenko et al. |
| 2016/0132732 A1* | 5/2016 | Gunther .......... G06K 9/00342 382/103 |
| 2016/0143567 A1 | 5/2016 | De Haan et al. |
| 2016/0143580 A1 | 5/2016 | Wood et al. |
| 2016/0148531 A1 | 5/2016 | Bleich et al. |
| 2016/0150582 A1 | 5/2016 | Jung et al. |
| 2016/0150978 A1 | 6/2016 | Yuen et al. |
| 2016/0155006 A1 | 6/2016 | Makkapati et al. |
| 2016/0157739 A1 | 6/2016 | Peeters et al. |
| 2016/0157761 A1 | 6/2016 | De Haan |
| 2016/0166156 A1 | 6/2016 | Yuen et al. |
| 2016/0171684 A1 | 6/2016 | De Haan |
| 2016/0183818 A1 | 6/2016 | Richards et al. |
| 2016/0191822 A1 | 6/2016 | Kosugou |
| 2016/0196635 A1 | 7/2016 | Cho et al. |
| 2016/0206216 A1 | 7/2016 | Kirenko |
| 2016/0206875 A1 | 7/2016 | Arnold et al. |
| 2016/0225346 A1 | 8/2016 | Choi |
| 2016/0235983 A1 | 8/2016 | Berman et al. |

(56) References Cited

U.S. PATENT DOCUMENTS

| | | |
|---|---|---|
| 2016/0246940 A1 | 8/2016 | Jain et al. |
| 2016/0246944 A1 | 8/2016 | Jain et al. |
| 2016/0262625 A1 | 9/2016 | Lawrenson et al. |
| 2016/0262691 A1 | 9/2016 | Jain et al. |
| 2016/0267732 A1 | 9/2016 | Agrafioti et al. |
| 2016/0300471 A1 | 10/2016 | Hwang et al. |
| 2016/0302674 A1 | 10/2016 | Moyer et al. |
| 2016/0302679 A1 | 10/2016 | De Haan |
| 2016/0302706 A1 | 10/2016 | Richards et al. |
| 2016/0303334 A1 | 10/2016 | Wood et al. |
| 2016/0317049 A1 | 11/2016 | LeBoeuf et al. |
| 2016/0317096 A1 | 11/2016 | Adams et al. |
| 2016/0317097 A1 | 11/2016 | Adams et al. |
| 2016/0321401 A1 | 11/2016 | Buil et al. |
| 2016/0325143 A1 | 11/2016 | Yuen et al. |
| 2016/0331991 A1 | 11/2016 | Kirenko |
| 2016/0338604 A1 | 11/2016 | Wang et al. |
| 2016/0342905 A1 | 11/2016 | Ghose et al. |
| 2016/0343130 A1 | 11/2016 | Wang et al. |
| 2016/0343135 A1 | 11/2016 | De Haan et al. |
| 2016/0349790 A1 | 12/2016 | Connor |
| 2016/0349936 A1 | 12/2016 | Cho et al. |
| 2016/0360100 A1 | 12/2016 | Kim et al. |
| 2016/0371555 A1 | 12/2016 | Derakhshani et al. |
| 2016/0374578 A1 | 12/2016 | Kacelenga et al. |
| 2016/0375306 A1 | 12/2016 | Gu et al. |
| 2016/0378069 A1 | 12/2016 | Rothkopf |
| 2016/0378070 A1 | 12/2016 | Rothkopf |
| 2016/0378071 A1 | 12/2016 | Rothkopf |
| 2016/0378608 A1 | 12/2016 | Kong et al. |
| 2016/0381534 A1 | 12/2016 | Kwon et al. |
| 2017/0000359 A1 | 1/2017 | Kohli et al. |
| 2017/0007189 A1 | 1/2017 | De Haan et al. |
| 2017/0010675 A1 | 1/2017 | Lee et al. |
| 2017/0011210 A1 | 1/2017 | Cheong et al. |
| 2017/0014037 A1 | 1/2017 | Coppola et al. |
| 2017/0014087 A1 | 1/2017 | Verkruijsse et al. |
| 2017/0020449 A1 | 1/2017 | Shim et al. |
| 2017/0027523 A1 | 2/2017 | Venkatraman et al. |
| 2017/0032168 A1 | 2/2017 | Kim |
| 2017/0040675 A1 | 2/2017 | Sakong et al. |
| 2017/0042432 A1 | 2/2017 | Adib et al. |
| 2017/0049391 A1 | 2/2017 | Melker |
| 2017/0055572 A1 | 3/2017 | Utley et al. |
| 2017/0055573 A1 | 3/2017 | Utley et al. |
| 2017/0055853 A1 | 3/2017 | Kirenko et al. |
| 2017/0055900 A1 | 3/2017 | Jain et al. |
| 2017/0060521 A1 | 3/2017 | Cellier et al. |
| 2017/0060927 A1 | 3/2017 | Cellier et al. |
| 2017/0075426 A1 | 3/2017 | Camacho Perez et al. |
| 2017/0079530 A1 | 3/2017 | DiMaio et al. |
| 2017/0079534 A1 | 3/2017 | Tchertkov et al. |
| 2017/0079535 A1 | 3/2017 | Tchertkov et al. |
| 2017/0084983 A1 | 3/2017 | Baringer et al. |
| 2017/0086755 A1 | 3/2017 | De Haan |
| 2017/0095170 A1 | 4/2017 | Verkruijsse et al. |
| 2017/0095721 A1 | 4/2017 | Bleich et al. |
| 2017/0100637 A1 | 4/2017 | Princen et al. |
| 2017/0112381 A1 | 4/2017 | Kumar et al. |
| 2017/0112382 A1 | 4/2017 | Nakata et al. |
| 2017/0112445 A1 | 4/2017 | Wang et al. |
| 2017/0112447 A1 | 4/2017 | Aumer et al. |
| 2017/0112671 A1 | 4/2017 | Goldstein |
| 2017/0118640 A1 | 4/2017 | Lee et al. |
| 2017/0119304 A1 | 5/2017 | Jeanne |
| 2017/0119314 A1 | 5/2017 | Just et al. |
| 2017/0119315 A1 | 5/2017 | LeBoeuf et al. |
| 2017/0119318 A1 | 5/2017 | Shay et al. |
| 2017/0127988 A1 | 5/2017 | Tao et al. |
| 2017/0131714 A1 | 5/2017 | Boesch et al. |
| 2017/0132786 A1 | 5/2017 | Cheng et al. |
| 2017/0135636 A1 | 5/2017 | Park et al. |
| 2017/0142244 A1 | 5/2017 | Jeong et al. |
| 2017/0142589 A1 | 5/2017 | Park et al. |
| 2017/0160398 A1 | 6/2017 | Venkatraman et al. |
| 2017/0160819 A1 | 6/2017 | Yi et al. |
| 2017/0169714 A1 | 6/2017 | Lin et al. |
| 2017/0172434 A1 | 6/2017 | Amelard et al. |
| 2017/0185737 A1 | 6/2017 | Kovacs |
| 2017/0188864 A1 | 7/2017 | Drury |
| 2017/0188893 A1 | 7/2017 | Venkatraman et al. |
| 2017/0196497 A1 | 7/2017 | Ray et al. |
| 2017/0199974 A1 | 7/2017 | Chun et al. |
| 2017/0202505 A1 | 7/2017 | Kirenko et al. |
| 2017/0209053 A1 | 7/2017 | Pantelopoulos et al. |
| 2017/0209055 A1 | 7/2017 | Pantelopoulos et al. |
| 2017/0212999 A1 | 7/2017 | Wang |
| 2017/0238847 A1 | 8/2017 | Inan et al. |
| 2017/0245759 A1 | 8/2017 | Jain et al. |
| 2017/0245766 A1 | 8/2017 | Flower et al. |
| 2017/0245768 A1 | 8/2017 | White et al. |
| 2017/0246086 A1 | 8/2017 | Jain et al. |
| 2017/0249438 A1 | 8/2017 | Jain et al. |
| 2017/0249445 A1 | 8/2017 | Devries et al. |
| 2017/0257162 A1 | 9/2017 | Panther et al. |
| 2017/0274267 A1 | 9/2017 | Blahnik |
| 2017/0278313 A1 | 9/2017 | Maslar et al. |
| 2017/0280394 A1 | 9/2017 | Kim et al. |
| 2017/0281026 A1 | 10/2017 | Nick et al. |
| 2017/0281050 A1 | 10/2017 | Noguchi et al. |
| 2017/0312612 A1 | 11/2017 | Bleich et al. |
| 2017/0316419 A1 | 11/2017 | Laporta |
| 2017/0319073 A1 | 11/2017 | DiMaio et al. |
| 2017/0319114 A1 | 11/2017 | Kaestle |
| 2017/0323485 A1 | 11/2017 | Samec et al. |
| 2017/0325680 A1 | 11/2017 | Ogino et al. |
| 2017/0325686 A9 | 11/2017 | Shan et al. |
| 2017/0332968 A1 | 11/2017 | Salo et al. |
| 2017/0337742 A1 | 11/2017 | Powderly et al. |
| 2017/0339337 A1 | 11/2017 | Kim et al. |
| 2017/0344713 A1 | 11/2017 | Riistama et al. |
| 2017/0344793 A1 | 11/2017 | Xue et al. |
| 2017/0346817 A1 | 11/2017 | Gordon et al. |
| 2017/0357217 A1 | 12/2017 | Raymann et al. |
| 2017/0357419 A1 | 12/2017 | Raymann et al. |
| 2017/0357868 A1 | 12/2017 | Derakhshani et al. |
| 2017/0358239 A1 | 12/2017 | Arney et al. |
| 2017/0358240 A1 | 12/2017 | Blahnik et al. |
| 2017/0359635 A1 | 12/2017 | Aumer et al. |
| 2017/0360340 A1 | 12/2017 | De Haan |
| 2017/0360374 A1 | 12/2017 | Elliott et al. |
| 2017/0361759 A1 | 12/2017 | Kim |
| 2017/0365101 A1 | 12/2017 | Samec et al. |
| 2017/0366213 A1 | 12/2017 | Camacho Perez et al. |
| 2017/0367580 A1 | 12/2017 | DiMaio et al. |
| 2017/0367590 A1 | 12/2017 | Sebe et al. |
| 2017/0372312 A1 | 12/2017 | Laporta |
| 2018/0000367 A1 | 1/2018 | Longinotti-Buitoni |
| 2018/0005625 A1 | 1/2018 | Han |
| 2018/0014736 A1 | 1/2018 | Misharin |
| 2018/0020155 A1 | 1/2018 | Kim et al. |
| 2018/0021217 A1 | 1/2018 | Tracey et al. |
| 2018/0028122 A1 | 2/2018 | Golda et al. |
| 2018/0042486 A1 | 2/2018 | Yoshizawa et al. |
| 2018/0042513 A1 | 2/2018 | Connor |
| 2018/0042526 A1 | 2/2018 | Hong et al. |
| 2018/0049654 A1 | 2/2018 | Melker et al. |
| 2018/0082474 A1 | 3/2018 | Vaughn et al. |
| 2018/0085055 A1 | 3/2018 | Annoni et al. |
| 2018/0101138 A1 | 4/2018 | Raymann et al. |
| 2018/0106897 A1 | 4/2018 | Shouldice et al. |
| 2018/0116532 A1 | 5/2018 | Han et al. |
| 2018/0140255 A1 | 5/2018 | Tao et al. |
| 2018/0153455 A1 | 6/2018 | Guazzi et al. |
| 2018/0177459 A1 | 6/2018 | Eletr et al. |
| 2018/0177463 A1 | 6/2018 | Addison et al. |
| 2018/0184899 A1 | 7/2018 | Visconti |
| 2018/0184920 A1 | 7/2018 | Rabinovich et al. |
| 2018/0184923 A1 | 7/2018 | Tal et al. |

(56) References Cited

U.S. PATENT DOCUMENTS

2018/0199837 A1 7/2018 Aumer et al.
2018/0214088 A1 8/2018 Newberry

OTHER PUBLICATIONS

A. Asthana, S. Zafeiriou, S. Cheng, and M. Pantic. Robust discriminative response map fitting with constrained local models. In CVPR, 2013.
G. Balakrishnan, F. Durand, and J. Guttag. Detecting pulse from head motions in video. In CVPR, 2013.
S. Boyd, N. Parikh, E. Chu, B. Peleato, and J. Eckstein. Distributed optimization and statistical learning via the alternating direction method of multipliers. Foundations and Trends in Machine Learning, 3(1):1-122, 2011.
R. Cabral, F. De la Tone, J. P. Costeira, and A. Bernardino. Matrix completion for weakly-supervised multi-label image classification. IEEE TPAMI, 37(1):121-135, 2015.
J.-F. Cai, E. J. Cande's, and Z. Shen. A singular value thresholding algorithm for matrix completion. SIAM Journal on Optimization, 20(4):1956-1982, 2010.
E. J. Cande's and B. Recht. Exact matrix completion via convex optimization. Foundations of Computational mathematics, 9(6):717-772, 2009.
C.-H. Chen, V. M. Patel, and R. Chellappa. Matrix completion for resolving label ambiguity. In CVPR, 2015.
G. De Haan and V. Jeanne. Robust pulse rate from chrominance-based rPPG. IEEE Transaction on Biomedical Engineering, 60(10):2878-2886, 2013.
A. Goldberg, B. Recht, J. Xu, R. Nowak, and X. Zhu. Transduction with matrix completion: Three birds with one stone. In NIPS, 2010.
A. Jeni, J. F. Cohn, and T. Kanade. Dense 3D Face Alignment from 2D Videos in Real-Time. In FG, 2015.
A. Jourabloo and X. Liu. Pose-Invariant 3D Face Alignment. In ICCV, 2015.
V. Kalofolias, X. Bresson, M. Bronstein, and P. Vandergheynst. Matrix completion on graphs. In NIPS Workshops, 2014.
A. Kovnatsky, M. M. Bronstein, X. Bresson, and P. Vandergheynst. Functional correspondence by matrix completion. CVPR, 2015.
X. Li, J. Chen, G. Zhao, and M. Pietikainen. Remote Heart Rate Measurement From Face Videos Under Realistic Situations. In CVPR, 2014.
M.-Z. Poh, D. J. McDuff, and R. W. Picard. Non-contact, automated cardiac pulse measurements using video imaging and blind source separation. Optics express, 18(10):10762-10774, 2010.
M. Z. Poh, D. J. McDuff, and R. W. Picard. Advancements in noncontact, multiparameter physiological measurements using a webcam. IEEE Transactions on Biomedical Engineering, 58.1 (2011): 7-11.
M. Soleymani, J. Lichtenauer, T. Pun, and M. Pantic. A multimodal database for affect recognition and implicit tagging. IEEE Transaction on Affective Computing, 3, 2012.
S. Tulyakov and N. Sebe. Regressing a 3D face shape from a single image. In ICCV, 2015.
G. Valenza, L. Citi, A. Lanata', E. P. Scilingo, and R. Barbieri. Revealing real-time emotional responses: a personalized assessment based on heartbeat dynamics. Scientific reports, 2015.
W. Verkruysse, L. O. Svaasand, and J. S. Nelson. Remote plethysmographic imaging using ambient light. Optics Ex- press, 16(26):21434, 2008.
W. Wang, Z. Cui, Y. Yan, J. Feng, S. Yan, X. Shu, and N. Sebe. Recurrent face aging. In CVPR, 2016.
W. Wang, S. Stuijk, and G. D. Haan. Exploiting Spatial Redundancy of Image Sensor for Motion Robust rPPG. IEEE Transactions on Biomedical Engineering, 62(2):415-425, 2015.
P. D. Welch. The use of fast fourier transform for the estimation of power spectra: A method based on time averaging over short, modified periodograms. IEEE Transactions on Audio and Electroacoustics, 15(2):70-73, 1967.
H.-Y. Wu, M. Rubinstein, E. Shih, J. Guttag, F. Durand, and W. Freeman. Eulerian video magnification for revealing subtle changes in the world. In ACM Transactions on Graphics, 2012.
L. Wu, R. Jin, and A. K. Jain. Tag completion for image retrieval. IEEE TPAMI, 35(3):716-727, 2013.
X. Xiong and F. De La Tone. Supervised descent method and its applications to face alignment. In CVPR, 2013.
S. Xu, L. Sun, and G. K. Rohde. Robust efficient estimation of heart rate pulse from video. Biomedical optics express, 5:1124-35, 2014.
X. Zhang, L. Yin, J. F. Cohn, S. Canavan, M. Reale, and A. Horowitz. A high-resolution spontaneous 3D dynamic facial expression database. In FG, 2013.
Z. Zhang, J. Girard, Y. Wu, X. Zhang, P. Liu, U. Ciftci, S. Canavan, M. Reale, A. Horowitz, H. Yang, J. F. Cohn, Q. Ji, and L. Yin. Multimodal spontaneous emotion corpus for human behavior analysis. In CVPR, 2016.
Akçakaya, M., Basha, T.A., Goddu, B., Goepfert, L.A., Kissinger, K.V., Tarokh, V., Manning, W.J. and Nezafat, R., 2011. Low-dimensional-structure self-learning and thresholding: Regularization beyond compressed sensing for MRI Reconstruction. Magnetic Resonance in Medicine, 66(3), pp. 756-767.
Alameda-Pineda, X. , Y. Yan, E. Ricci, and N. Sebe. Recognizing emotions from abstract paintings using non-linear matrix completion. In CVPR, 2016. 3.
Allen, John. "Photoplethysmography and its application in clinical physiological measurement." Physiological measurement 28.3 (2007): R1.
Bhojanapalli, S., Sanghavi, E.S. and Ward, R., 2014. Coherent matrix completion. www.jmlr.org/proceedings/papers/v32/chenc14.pdf.
Bolkhovsky, Jeffrey B., Christopher G. Scully, and Ki H. Chon. "Statistical analysis of heart rate and heart rate variability monitoring through the use of smart phone cameras." 2012 Annual International Conference of the IEEE Engineering in Medicine and Biology Society. IEEE, 2012.
Bousefsaf, Frédéric, Choubeila Maaoui, and Alain Pruski. "Continuous wavelet filtering on webcam photoplethysmographic signals to remotely assess the instantaneous heart rate." Biomedical Signal Processing and Control 8.6 (2013): 568-574.
Cai, J.F., Candès, E.J. and Shen, Z., 2010. A singular value thresholding algorithm for matrix completion. SIAM Journal on Optimization, 20(4), pp. 1956-1982.
Cai, T.T. and Zhou, W.X., 2016. Matrix completion via max-norm constrained optimization. Electronic Journal of Statistics, 10(1), pp. 1493-1525.
Candes, Emmanuel J., and Yaniv Plan. "Matrix completion with noise." Proceedings of the IEEE 98, No. 6 (2010): 925-936.
Candes, E.J. and Plan, Y., 2011. Tight oracle inequalities for low-rank matrix recovery from a minimal number of noisy random measurements. IEEE Transactions on Information Theory, 57(4), pp. 2342-2359.
Candes, E. and Romberg, J., 2007. Sparsity and incoherence in compressive sampling. Inverse problems, 23(3), p. 969.
Chen, Jie, et al. "RealSense= real heart rate: Illumination invariant heart rate estimation from videos." Image Processing Theory Tools and Applications (IPTA), 2016 6th International Conference on. IEEE, 2016.
Chen, Ming-Xiang. "Deep Learning on Time-Frequency Representation for Heart Rate Estimation." (2017).
Cheng, J., Ye, Q., Jiang, H., Wang, D. and Wang, C., 2013. STCDG: an efficient data gathering algorithm based on matrix completion for wireless sensor networks. IEEE Transactions on Wireless Communications, 12(2), pp. 850-861.
Cheng, J., Jiang, H., Ma, X., Liu, L., Qian, L., Tian, C. and Liu, W., Dec. 2010. Efficient data collection with sampling in WSNs: making use of matrix completion techniques. In Global Telecommunications Conference (GLOBECOM 2010), 2010 IEEE (pp. 1-5). IEEE.
Chung, Dahjung, et al. "Improving Video-Based Heart Rate Estimation." Electronic Imaging 2016.19 (2016): 1-6.
Chwyl, Brendan, et al. "Time-frequency domain analysis via pulselets for non-contact heart rate estimation from remotely acquired photoplethysmograms." Computer and Robot Vision (CRV), 2016 13th Conference on. IEEE, 2016.

(56) References Cited

OTHER PUBLICATIONS

Fira, M., Goras, L. and Barabasa, C., Jul. 2013. Reconstruction of compressed sensed ECG signals using patient specific dictionaries. In Signals, Circuits and Systems (ISSCS), 2013 International Symposium on (pp. 1-4). IEEE.
Gao, H., Lin, H., Ahn, C.B. and Nalcioglu, O., 2011. PRISM: A divide-and-conquer low-rank and sparse decomposition model for dynamic MRI. UCLA CAM Report, pp. 11-26.
Gunther, J., N. Ruben and T. Moon, "Model-based (passive) heart rate estimation using remote video recording of moving human subjects illuminated by ambient light," Image Processing (ICIP), 2015 IEEE International Conference on, Quebec City, QC, 2015, pp. 2870-2874. doi: 10.1109/ICIP.2015.7351327.
Gupta, Otkrist, Dan McDuff, and Ramesh Raskar. "Real-Time Physiological Measurement and Visualization Using a Synchronized Multi-Camera System." Proceedings of the IEEE Conference on Computer Vision and Pattern Recognition Workshops. 2016.
Hamedani, Kian, Zahra Bahmani, and Amin Mohammadian. "Spatio-temporal filtering of thermal video sequences for heart rate estimation." Expert Systems with Applications 54 (2016): 88-94.
Hague, Mohammad Ahsanul, Kamal Nasrollahi, and Thomas B. Moeslund. "Multimodal Estimation of Heartbeat Peak Locations and Heartbeat Rate From Facial Video Using Empirical Mode Decomposition." Visual Analysis of Faces with Application in Biometrics, Forensics and Health Informatics (2016): 241.
Hague, Mohammad A., Kamal Nasrollahi, and Thomas B. Moeslund. "Estimation of Heartbeat Peak Locations and Heartbeat Rate from Facial Video." Scandinavian Conference on Image Analysis. Springer, Cham, 2017.
Hague, Mohammad A., et al. "Heartbeat rate measurement from facial video." IEEE Intelligent Systems 31.3 (2016): 40-48.
Hardt, M., 2013. On the provable convergence of alternating minimization for matrix completion. arXiv preprint arxiv:1312. 0925.
Hassner, T., S. Harel, E. Paz, and R. Enbar. Effective face frontalization in unconstrained images. In CVPR, 2015. 3.
Holton, Benjamin D., et al. "Signal recovery in imaging photoplethysmography." Physiological measurement 34.11 (2013): 1499.
Hu, P., Yang, S., Chen, H., Stansbury, L., Miller, C., Colton, K., Kalpakis, K., Fang, R. and Stein, D.M., 2013. Noninvasive Intracranial Pressure Monitoring Using Advanced Machine Learning Techniques (No. AFRL-SA-WP-TR-2013-0021). School of Aerospace Medicine Wright Patterson AFB OH.
Hsu, YungChien, Yen-Liang Lin, and Winston Hsu. "Learning-based heart rate detection from remote photoplethysmography features." 2014 IEEE International Conference on Acoustics, Speech and Signal Processing (ICASSP). IEEE, 2014.
Hu, Y., Zhang, D., Ye, J., Li, X. and He, X., 2013. Fast and accurate matrix completion via truncated nuclear norm regularization. IEEE transactions on pattern analysis and machine intelligence, 35(9), pp. 2117-2130.
Hu, Y., Zhang, D., Liu, J., Ye, J. and He, X., Aug. 2012. Accelerated singular value thresholding for matrix completion. In Proceedings of the 18th ACM SIGKDD international conference on Knowledge discovery and data mining (pp. 298-306). ACM.
Jain, Monika, Sujay Deb, and A. V. Subramanyam. "Face video based touchless blood pressure and heart rate estimation." Multimedia Signal Processing (MMSP), 2016 IEEE 18th International Workshop on. IEEE, 2016.
Jayadevappa, B. M., and Mallikarjun S. Holi. "An Estimation Technique using FFT for Heart Rate Derived from PPG Signal." (2015).
Ji, Hui, Chaoqiang Liu, Zuowei Shen, and Yuhong Xu. "Robust video denoising using low rank matrix completion." In CVPR, pp. 1791-1798. 2010.
Ji, H., Huang, S., Shen, Z. and Xu, Y., 2011. Robust video restoration by joint sparse and low rank matrix approximation. SIAM Journal on Imaging Sciences, 4(4), pp. 1122-1142.

Kamal, A. A. R., et al. "Skin photoplethysmography-a review." Computer methods and programs in biomedicine 28.4 (1989): 257-269.
Király, F., Theran, L. and Tomioka, R., 2015. The algebraic combinatorial approach for low-rank matrix completion. J Mach Learn Res, 16, pp. 1391-1436.
Klopp, O., Lafond, J., Moulines, É. and Salmon, J., 2015. Adaptive multinomial matrix completion. Electronic Journal of Statistics, 9(2), pp. 2950-2975.
Kranjec, Jure, et al. "Non-contact heart rate and heart rate variability measurements: A review." Biomedical Signal Processing and Control 13 (2014): 102-112.
Krishnamurthy, Akshay, and Aarti Singh. "Low-rank matrix and tensor completion via adaptive sampling." In Advances in Neural Information Processing Systems, pp. 836-844. 2013.
Kwon, Sungjun, Hyunseok Kim, and Kwang Suk Park. "Validation of heart rate extraction using video imaging on a built-in camera system of a smartphone." 2012 Annual International Conference of the IEEE Engineering in Medicine and Biology Society. IEEE, 2012.
Kyal, Survi. "Constrained independent component analysis for non-obtrusive pulse rate measurements using a webcam." (2013).
Lakens, Daniel. "Using a smartphone to measure heart rate changes during relived happiness and anger." T. Affective Computing 4.2 (2013): 238-241.
Lee, Anthony, and Younghyun Kim. "Photoplethysmography as a form of biometric authentication." SENSORS, 2015 IEEE. IEEE, 2015.
Lee, C.H., Arzeno, N. M., Ho, J.C., Vikalo, H. and Ghosh, J., Sep. 2012. An imputation-enhanced algorithm for ICU mortality prediction. In 2012 Computing in Cardiology (pp. 253-256). IEEE.
Lee, J-S., K-W. Lin, and J-L. Syue. "Smartphone-based heart-rate measurement using facial images and a spatiotemporal alpha-trimmed mean filter." Technology and Health Care 24.s2 (2016): S777-S783.
Lempe, Georg, et al. "ROI selection for remote photoplethysmography." Bildverarbeitung für die Medizin 2013. Springer Berlin Heidelberg, 2013. 99-103.
Lewandowska, Magdalena, et al. "Measuring pulse rate with a webcam—a non-contact method for evaluating cardiac activity." Computer Science and Information Systems (FedCSIS), 2011 Federated Conference on. IEEE, 2011.
Li, N. and Li, B., Sep. 2010. Tensor completion for on-board compression of hyperspectral images. In 2010 IEEE International Conference on Image Processing (pp. 517-520). IEEE.
Li, Xiaobai and Chen, Jie and Zhao, Guoying and Pietikainen, Matti, "Remote Heart Rate Measurement From Face Videos Under Realistic Situations", The IEEE Conference on Computer Vision and Pattern Recognition (CVPR), Jun. 2014.
Lin, Kuan-Yi, Duan-Yu Chen, and Wen-Jiin Tsai. "Face-Based Heart Rate Signal Decomposition and Evaluation Using Multiple Linear Regression." IEEE Sensors Journal 16.5 (2016): 1351-1360.
Lin, Zhouchen, Risheng Liu, and Zhixun Su. "Linearized alternating direction method with adaptive penalty for low-rank representation." In Advances in neural information processing systems, pp. 612-620. 2011.
Liu, R., Lin, Z. and Su, Z., Oct. 2013. Linearized alternating direction method with parallel splitting and adaptive penalty for separable convex programs in machine learning. In ACML (pp. 116-132).
Liu, Dongran, et al. Heart-Rate Monitoring Using Single Camera. No. 2017-01-1434. SAE Technical Paper, 2017.
Luo, Y., Liu, T., Tao, D. and Xu, C., 2015. Multiview matrix completion for multilabel image classification. IEEE Transactions on Image Processing, 24(8), pp. 2355-2368.
Majumdar, A. and Ward, R.K., 2011. Some empirical advances in matrix completion. Signal Processing, 91(5), pp. 1334-1338.
Malacarne, Alain, et al. "Improved remote estimation of heart rate in face videos." Signal and Information Processing (GlobalSIP), 2016 IEEE Global Conference on. IEEE, 2016.
Marjanovic, G. and Solo, V., 2012. On optimization and matrix completion. IEEE Transactions on signal processing, 60(11), pp. 5714-5724.

(56) References Cited

OTHER PUBLICATIONS

Mascaro, Stephen A., and H. Harry Asada. "Photoplethysmograph fingernail sensors for measuring finger forces without haptic obstruction." IEEE Transactions on robotics and automation 17.5 (2001): 698-708.

McDuff, Daniel, Sarah Gontarek, and Rosalind Picard. "Remote measurement of cognitive stress via heart rate variability." 2014 36th Annual International Conference of the IEEE Engineering in Medicine and Biology Society. IEEE, 2014.

McDuff, Daniel, Sarah Gontarek, and Rosalind W. Picard. "Improvements in remote cardiopulmonary measurement using a five band digital camera." IEEE Transactions on Biomedical Engineering 61.10 (2014): 2593-2601.

Melker, Richard J., Joachim S. Gravenstein, and George Worley. "Specially configured lip/cheek pulse oximeter/photoplethysmography probes, selectively with sampler for capnography, and covering sleeves for same." U.S. Pat. No. 7,127,278. Oct. 24, 2006.

Mishra, B., Apuroop, K.A. and Sepulchre, R., 2012. A Riemannian geometry for low-rank matrix completion. arXiv preprint arXiv:1211.1550.

Monkaresi, Hamed, et al. "Automated detection of engagement using video-based estimation of facial expressions and heart rate." IEEE Transactions on Affective Computing 8.1 (2017): 15-28.

Ngo, T. and Saad, Y., 2012. Scaled gradients on Grassmann manifolds for matrix completion. In Advances in Neural Information Processing Systems (pp. 1412-1420).

Othman, S.B., Trad, A. and Youssef, H., Aug. 2014. Security architecture for at-home medical care using Wireless Sensor Network. In 2014 International Wireless Communications and Mobile Computing Conference (IWCMC) (pp. 304-309). IEEE.

Poh, Ming-Zher, Daniel J. McDuff, and Rosalind W. Picard. "Non-contact, automated cardiac pulse measurements using video imaging and blind source separation." Optics express 18.10 (2010): 10762-10774.

Pursche, T., J. Krajewski, and Reinhard Moeller. "Video-based heart rate measurement from human faces." 2012 IEEE International Conference on Consumer Electronics (ICCE). IEEE, 2012.

Rapczynski, Michal, Philipp Werner, and Ayoub Al-Hamadi. "Continuous Low Latency Heart Rate Estimation from Painful Faces in Real Time." 23th International Conference on Pattern Recognition ICPR (accepted). 2016.

Recht, B. and Re, C., 2013. Parallel stochastic gradient algorithms for large-scale matrix completion. Mathematical Programming Computation, 5(2), pp. 201-226.

Recht, B., Fazel, M. and Parrilo, P.A., 2010. Guaranteed minimum-rank solutions of linear matrix equations via nuclear norm minimization. SIAM review, 52(3), pp. 471-501.

Resit Kaysaoğlu, A. et al., "A novel feature ranking algorithm for biometric recognition with PPG signals", Computers in Biology and Medicine, vol. 49, 1-14 (2014), dx.doi.org/10.1016/j.compbiomed.2014.03.005.

Roald, Nikolai Grov. "Estimation of vital signs from ambient-light non-contact photoplethysmography." (2013).

Ruben, Nathan E. Remote Heart Rate Estimation Using Consumer-Grade Cameras. Diss. Utah State University, 2015.

Schäfer, Axel, and Jan Vagedes. "How accurate is pulse rate variability as an estimate of heart rate variability?: A review on studies comparing photoplethysmographic technology with an electrocardiogram." International journal of cardiology 166.1 (2013): 15-29.

Scully, Christopher G., et al. "Physiological parameter monitoring from optical recordings with a mobile phone." IEEE Transactions on Biomedical Engineering 59.2 (2012): 303-306.

Shelley, Kirk H. "Photoplethysmography: beyond the calculation of arterial oxygen saturation and heart rate." Anesthesia & Analgesia 105.6 (2007): S31-S36.

Sikdar, Arindam, Santosh Kumar Behera, and Debi Prosad Dogra. "Computer-Vision-Guided Human Pulse Rate Estimation: A Review." IEEE reviews in biomedical engineering 9 (2016): 91-105.

Sun, Yu, et al. "Motion-compensated noncontact imaging photoplethysmography to monitor cardiorespiratory status during exercise." Journal of biomedical optics 16.7 (2011): 077010-077010.

Takahashi, Kazuhiko, Syota Maekawa, and Masafumi Hashimoto. "Active state recognition of a person by the multimodal biological information estimated from facial image sequences." Industrial Electronics Society, IECON 2016-42nd Annual Conference of the IEEE. IEEE, 2016.

Takano, Chihiro, and Yuji Ohta. "Heart rate measurement based on a time-lapse image." Medical engineering & physics 29.8 (2007): 853-857.

Tanner, J. and Wei, K., 2013. Normalized iterative hard thresholding for matrix completion. SIAM Journal on Scientific Computing, 35(5), pp. S104-S125.

Tarassenko, L., et al. "Non-contact video-based vital sign monitoring using ambient light and auto-regressive models." Physiological measurement 35.5 (2014): 807.

Tarbox, Elizabeth A., et al. "Motion correction for improved estimation of heart rate using a visual spectrum camera." SPIE Commercial+ Scientific Sensing and Imaging. International Society for Optics and Photonics, 2017.

Tasli, H. Emrah, Amogh Gudi, and Marten den Uyl. "Remote PPG based vital sign measurement using adaptive facial regions." 2014 IEEE International Conference on Image Processing (ICIP). IEEE, 2014.

Teflioudi, C., Makari, F. and Gemulla, R., Dec. 2012. Distributed matrix completion. In 2012 IEEE 12th International Conference on Data Mining (pp. 655-664). IEEE.

Todeschini, A., Caron, F. and Chavent, M., 2013. Probabilistic low-rank matrix completion with adaptive spectral regularization algorithms. In Advances in Neural Information Processing Systems (pp. 845-853).

Tsouri, Gill R., et al. "Constrained independent component analysis approach to nonobtrusive pulse rate measurements." Journal of biomedical optics 17.7 (2012): 0770111-0770114.

Tulyakov, Sergey, et al. "Self-adaptive matrix completion for heart rate estimation from face videos under realistic conditions." Proceedings of the IEEE Conference on Computer Vision and Pattern Recognition. 2016.

Wang, H., Zhao, R. and Cen, Y., 2014. Rank adaptive atomic decomposition for low-rank matrix completion and its application on image recovery. Neurocomputing, 145, pp. 374-380.

Wei, Lan, et al. "Automatic webcam-based human heart rate measurements using laplacian eigenmap." Asian Conference on Computer Vision. Springer Berlin Heidelberg, 2012.

www.marcoaltini.com/blog/heart-rate-variability-using-the-phones-camera.

Xie, K., Wang, L., Wang, X., Wen, J. and Xie, G., Jun. 2014. Learning from the past: intelligent on-line weather monitoring based on matrix completion. In Distributed Computing Systems (ICDCS), 2014 IEEE 34th International Conference on (pp. 176-185). IEEE.

Xu, Shuchang, Lingyun Sun, and Gustavo Kunde Rohde. "Robust efficient estimation of heart rate pulse from video." Biomedical optics express 5.4 (2014): 1124-1135.

Yadhuraj, S. R., and H. Harsha. "Motion Artifact Reduction in Photoplethysmographic Signals: A Review." International Journal of Innovative Research and Development‖ ISSN 2278-0211 2.3 (2013): 626-640.

Yan, M., Yang, Y. and Osher, S., 2013. Exact low-rank matrix completion from sparsely corrupted entries via adaptive outlier pursuit. Journal of Scientific Computing, 56(3), pp. 433-449.

Yan, Bryan P., et al. "Resting and Postexercise Heart Rate Detection From Fingertip and Facial Photoplethysmography Using a Smartphone Camera: A Validation Study." JMIR mHealth and uHealth 5.3 (2017).

Yang, S., Kalpakis, K., Mackenzie, C.F., Stansbury, L.G., Stein, D.M., Scalea, T.M. and Hu, P.F., Dec. 2012. Online recovery of missing values in vital signs data streams using low-rank matrix completion. In Machine Learning and Applications (ICMLA), 2012 11th International Conference on (vol. 1, pp. 281-287). IEEE.

(56) References Cited

OTHER PUBLICATIONS

Yu, Yong-Poh, et al. "Video-based heart rate measurement using short-time Fourier transform." Intelligent Signal Processing and Communications Systems (ISPACS), 2013 International Symposium on. IEEE, 2013.

Yu, Yong Poh. Dynamic heart rate estimation using facial images from video sequences/Yu Yong Poh. Diss. University of Malaya, 2016.

Zhang, Z., Z. Pi and B. Liu, "TROIKA: A General Framework for Heart Rate Monitoring Using Wrist-Type Photoplethysmographic Signals During Intensive Physical Exercise," in IEEE Transactions on Biomedical Engineering, vol. 62, No. 2, pp. 522-531, Feb. 2015. doi: 10.1109/TBME.2014.2359372.

Zhao, B., Haldar, J.P., Christodoulou, A.G. and Liang, Z.P., 2012. Image reconstruction from highly undersampled-space data with joint partial separability and sparsity constraints. IEEE transactions on medical imaging, 31(9), pp. 1809-1820.

sourceforge.net/projects/pulsecapture/.

* cited by examiner

SELF-ADAPTIVE MATRIX COMPLETION FOR HEART RATE ESTIMATION FROM FACE VIDEOS UNDER REALISTIC CONDITIONS

CROSS REFERENCE TO RELATED APPLICATIONS

This application claims benefit of priority under 35 U.S.C. § 119(e) from U.S. Provisional Patent Application No. 62/354,475, filed Jun. 24, 2016, which is expressly incorporated by reference in its entirety.

GOVERNMENT RIGHTS

This invention was made with government support under CNS-1205664 and CNS-1205195 awarded by the National Science Foundation. The Government has certain rights in the invention.

BACKGROUND OF THE INVENTION

After being shown in [Verkruysse2008, Poh2010] that changes invisible to the naked eye can be used to estimate the heart rate from a video of human skin, this topic has attracted a lot of attention in the computer vision community. These subtle changes encompass both color [Wu2012] and motion [Balakrishnan2013] and they are induced by the internal functioning of the heart. Since faces appear frequently in videos and due to recent and significant improvements in face tracking and alignment methods [Asthana2013, Tulyakov2015, Jeni2015, Jourabloo2015, Xiong2013], facial-based remote heart rate estimation has recently become very popular [Li2014, Xu2014, DeHaan2013, Wang2015].

Classical approaches successfully addressed this problem under laboratory-controlled conditions, i.e. imposing constraints on the subject's movements and requiring the absence of facial expressions and mimics [Poh2010, Wu2012, Balakrishnan2013]. Therefore, such methods may not be suitable for real world applications, such as monitoring drivers inside a vehicle or people exercising. Long-time analysis constitutes a further limitation of existing works [Li2014, Poh2010, Poh2011]. Indeed, instead of estimating the instantaneous heart rate, they provide the average HR measurement over a long video sequence. The main disadvantage of using a long analysis window is the inability to capture interesting short-time phenomena, such as a sudden HR increase/decrease due to specific emotions [Valenza2014revealing].

In practice, another problem faced by researchers developing automatic HR measurement approaches, is the lack of publicly available datasets recorded under realistic conditions. A notable exception is the MAHNOB-HCI dataset [Soleymani2012], a multimodal dataset for research on emotion recognition and implicit tagging, which also contains HR annotations. Importantly, an extensive evaluation of existing HR measurement methods on MAHNOB-HCI have been performed by Li et al. [Li2014]. However, the MAHNOB-HCI dataset suffers from some limitations, since the recording conditions are quite controlled: most of the video sequences do not contain spontaneous facial expressions, illumination changes or large target movements [Li2014].

HR Estimation from Face Videos

Cardiac activity measurement is an essential tool to control the subjects' health and is actively used by medical practitioners. Conventional contact methods offer high accuracy of cardiac cycle. However, they require specific sensors to be attached to the human skin, be it a set of electrocardiogram (ECG) leads, a pulse oximeter, or the more recent fitness tracker. To avoid the use of invasive sensors, non-contact remote HR measurement from visual data has been proposed recently by computer vision researchers.

Verkruysse et al. [Verkruysse2008] showed that ambient light and a consumer camera can be used to reveal the cardio-vascular pulse wave and to remotely analyze the vital signs of a person. Poh et al. [Poh2010] proposed to use blind source separation on color changes caused by heart activity to extract the HR signal from a face video. In [Wu2012] an Eulerian magnification method is used to amplify subtle changes in a video stream and to visualize temporal dynamics of the blood flow. Balakrishnan et al. [Balakrishnan2013] showed that subtle head motions are affected by cardiac activity, and these motions can be used to extract HR measurements from a video stream.

However, all these methods failed to address the problems of HR estimation in presence of facial expressions and subject's movements, despite their frequent presence in real-world applications. This limits the use of these approaches to laboratory settings. In [DeHaan2013, Wang2015] a chrominance-based method to relax motion constraints was introduced. However, this approach was tested on a few not-publicly-available sequences, making it hard to compare with. Li et al. [Li2014] proposed an approach based on adaptive filtering to handle illumination and motion issues and they evaluated it on the publicly available MAHNOB-HCI dataset [Soleymani2012]. However, although this work represents a valuable step towards remote HR measurement from visual data, it also shares several major limitations with the previous methods. The output of the method is the average HR, whereas to capture short-term phenomena (e.g. HR variations due to instantaneous emotions) the processing of smaller time intervals is required. A further limitation of [Li2014] is the MAHNOB-HCI dataset itself, since it is collected in a laboratory setting and the subjects are required to wear an invasive EEG measuring device on their head. Additionally, subjects perform neither large movements nor many spontaneous facial expressions.

SUMMARY OF THE INVENTION

The aforementioned problems are addressed by introducing a novel approach for HR estimation from face videos, with higher accuracy than the state-of-the-art approaches and of robustly operating on short time sequences in order to detect the instantaneous HR. An extensive evaluation on two datasets: the MAHNOB-HCI, previously used for HR recognition research [Li2014], and a spontaneous dataset with heart rate data and RGB videos (named MMSE-HR), which is a subset of the larger multimodal spontaneous emotion corpus (MMSE) [Zhang2016] specifically targeted to challenge HR estimation methods, is performed. While previous works [Li2014, Wang2015] have acknowledged the importance of selecting parts of the signal to cope with noise and provide robust HR estimates, the present technology tackles this problem within a principled optimization framework.

The face is tracked in a given video sequence, so to follow rigid head movements [Li2014], and extract chrominance features [DeHaan2013] to compensate for illumination variations. Importantly, most previous approaches preselect a face region of interest (ROI) that is kept constant through the entire HR estimation. However, the region containing useful features for HR estimation is a priori different for every frame since major appearance changes are spatially and temporally localized (See FIG. 1). Therefore, a principled data-driven approach to automatically detect the face parts useful for HR measurement is provided, that estimates the time-varying mask of useful observations, selecting at each frame the relevant face regions from the chrominance features themselves.

Recent advances on matrix completion (MC) theory [Goldberg2010] have shown the ability to recover missing entries of a matrix that is partially observed, i.e. masked. The matrix completion-based learning algorithm is able to self-adapt, that is to automatically select the useful observations, and call it self-adaptive matrix completion (SAMC). Intuitively, while learning the mask allows us to discard those face regions strongly affected by facial expressions or large movements, completing the matrix smooths out the smaller noise associated to the chrominance feature extraction procedure. The experiments conducted on the MANHOB-HCI dataset clearly show that the present method outperforms the state-of-the-art approaches for HR prediction. To further demonstrate the ability of the present method to operate in challenging scenarios, a series of tests on the MMSE-HR dataset are provided, where subjects show significant movements and facial expressions.

The present technology addresses the problem of HR estimation from face videos in realistic conditions. To cope with large facial variations due to spontaneous facial expressions and movements, a principled framework is provided to automatically discard the face regions corresponding to noisy features and only use the reliable ones for HR prediction. The region selection is addressed within a novel matrix completion-based optimization framework, called self-adaptive matrix completion, for which an efficient solver is proposed.

The approach is demonstrated to be more accurate than previous methods for average HR estimation on publicly available benchmarks. In addition, short-term analysis results show the ability of the present method to detect instantaneous heart rate.

Extensive evaluations performed on the commonly used MAHNOB-HCI dataset and a spontaneous MMSE-HR dataset including 102 sequences of 40 subjects, moving and performing spontaneous facial expressions show advantages of the present technology. As shown, this dataset is valuable for instantaneous HR estimation.

It is therefore an object to provide a method of determining heart rate through by observation of a human face, comprising: acquiring a time series of images of a human face, wherein the time series of images are subject to variations between respective images of the time series in illumination and facial movements; adaptively selecting a subset of the regions of interest that exhibit a reliable heart-rate-determined variation; based at least on the heart-rate-determined variation, determining a heart rate and updating the adaptively selected subset of the regions of interest that exhibit the reliable heart-rate-determined variation; and outputting a signal corresponding to the determined heart rate.

The regions of interest may be selected according to at least matrix completion theory. The heart rate may be determined based on at least matrix completion theory.

The selected subset may be selected dependent on at least a noise parameter of respective features of the time series of images. The selected subset may be selected dependent on at least a movement of the human face represented in the time series of images. The selected subset may be selected dependent on at least changes represented in the time series of images which represent human facial expressions.

The method may further comprise tracking the face in the series of video images to follow rigid head movements.

The method may further comprise detecting chrominance features from the time series of images comprising video images, and assessing the heart rate-determined variation based on the detected chrominance features.

The adaptively selected subset of the regions of interest may exhibit the reliable heart-rate-determined variation through an entire period of heart rate estimation.

The reliable heart-rate-determined variation may be a variation in chrominance.

The heart rate may be determined in a process employing a cardiac cycle responsive filter.

The method may further comprise simultaneously recovering an unknown low-rank matrix and an underlying data mask, corresponding to most reliable heart-rate-determined variation observations of the human face.

It is therefore an object to provide a method of determining heart rate through by observation of a human face through a video camera, comprising: acquiring a series of video images of a human face, subject to variations in illumination and facial movements; analyzing the human face to determine regions of interest; adaptively selecting a subset of the regions of interest that exhibit a reliable heart-rate-determined variation in chrominance; based on the heart-rate-determined variation in chrominance, determining a heart rate and updating the subset of the regions of interest that exhibit the reliable heart-rate-determined variation in chrominance; and outputting a signal corresponding to the determined heart rate. The regions of interest may be selected according to matrix completion theory.

It is also an object to provide a method of determining heart rate of a human, comprising: acquiring a series of video images of a face of the human, the video images being subject to variations in illumination and facial movements; analyzing the human face to determine a plurality of regions; selecting a subset of the plurality of regions that have a reliable heart-rate-determined variation; based on the heart-rate-determined variation, updating the subset of the plurality of regions that have the reliable heart-rate-determined variation; and outputting a signal corresponding to the heart rate. The selected subset may exclude noisy features. The selected subset may exclude features which have visual characteristics that changed due to human spontaneous movement. The selected subset may exclude features which have visual characteristics that changed due to human facial expressions.

The method may further comprise tracking the face in the series of video images to follow rigid head movements.

The method may further comprise detecting chrominance features from the series of video images, and assessing the heart rate-determined variation based on the extracted detected features.

The selected subset of the plurality of regions preferably have the reliable heart-rate-determined variation through an entire period of heart rate estimation.

The updating the subset of the plurality of regions and determining the signal corresponding to the heart rate may be based on matrix completion theory.

The signal corresponding to the heart rate may be determined in a process employing a cardiac cycle responsive filter.

The method may further comprise simultaneously recovering an unknown low-rank matrix and an underlying data mask, corresponding to most reliable heart-rate-determined variation observations of the face.

It is also an object to provide a method of determining heart rate from video images, comprising: processing a stream of video images of a face to extract face regions; computing chrominance features of the face regions; jointly estimating an underlying low-rank feature matrix and a mask of reliable face regions, using a self-adaptive matrix completion algorithm; and computing the heart rate from a signal estimate provided by the self-adaptive matrix completion algorithm.

The processing may comprise warping a representation of the face into rectangles using a piece-wise linear warping procedure, and dividing rectangles into a grid containing a plurality of regions.

The method may further comprise selecting a subset of the plurality of regions that are robust to facial movements and expressions, while being sufficiently discriminant to account for changes in skin color responsive to cardiac cycle variation.

The computing of chrominance features may comprise: for each pixel, computing a chrominance signal C as a linear combination of two signals $X_f$ and $Y_f$, such that $C = X_f - \alpha Y_f$, where $$\alpha = \frac{\sigma(X_f)}{\sigma(Y_f)}$$

and $\sigma(X_f)$, $\sigma(Y_f)$ denote the standard deviations of $X_f$, $Y_f$; band-pass filtering signals the signals X and Y to obtain $X_f$, $Y_f$ respectively, where $X = 3R_n - 2G_n$, $Y = 1.5R_n + G_n - 1.5B_n$ and $R_n$, $G_n$ and $B_n$ are the normalized values of the individual color channels, wherein the color combination coefficients to derive X and Y are computed using a skin-tone standardization approach; and, for each region $r = 1, \ldots, R$, computing the final chrominance features averaging the values of the chrominance signals over all the pixels.

The jointly estimating may comprise enforcing a detection of chrominance feature variations that occur within a heart-rate frequency range. The jointly estimating may comprise masking extracted regions of the face dependent on at least facial movement dependent changes. The jointly estimating may comprise determining a local standard deviation over time of each extracted region of the face. The jointly estimating may comprise employing an alternating direction method of multipliers (ADMM), which solves an optimization problem by alternating a direction of the optimization while keeping other directions fixed.

The solving may comprise alternating the following three steps until convergence:

E/M-step
with fixed F and Z, obtaining optimal values of E and M by solving:

$$\min_E \nu \|E\|_* + \frac{\rho}{2} \|E - F + \rho^{-1} Z\|_{\mathcal{F}}^2. \quad (6)$$

$$\min_M \|M^\circ (F - C)\|_{\mathcal{F}}^2 - \beta \|M\|_1 + \mu \|M - \tilde{M}\|_{\mathcal{F}}^2 \quad (8)$$

F-step
with fixed E, Z and M, determining the optimal value of F by solving:

$$\min_F \|M^\circ (F - C)\|_{\mathcal{F}}^2 + \gamma Tr(FLF^T) + \frac{\rho}{2} \|F - E - \rho^{-1} Z\|_{\mathcal{F}}^2 \quad (11)$$

Z-step
determining value of Z:

$$Z^* = Z + \rho(E - F), \quad (14)$$

where the right-hand side represent the current values.

The largest singular value of E, which encodes the heart rate information, may be determined.

It is a further object to provide a system for determining cardiac contraction timing from video images, comprising: an input port configured to receive a time sequence of images of a human face; at least one automated processor, configured to: process a time sequence of images of the human face to extract facial regions; compute heartbeat-induced time-varying features of the facial regions; determine a respective statistical parameter for heartbeat-induced time-varying features of the respective facial regions; and compute a cardiac contraction timing based on at least the respective heartbeat-induced time-varying features of the respective facial regions and the determined statistical parameter for respective heartbeat-induced time-varying features of the respective facial regions; and an output port configured to convey a signal responsive to the cardiac contraction timing.

It is another object to provide a system for determining cardiac contraction timing from video images, comprising: an input port configured to receive a stream of video images of a face; at least one automated processor, configured to: process a stream of video images of the face to extract facial regions; computing chrominance features of the facial regions; jointly estimate an underlying low-rank feature matrix and a mask of reliable facial regions, using a self-adaptive matrix completion algorithm; and compute the cardiac contraction timing from a signal estimate provided by the self-adaptive matrix completion algorithm; and an output port configured to convey a signal responsive to the cardiac contraction timing.

The at least one automated processor may be further configured to process the stream of video images by warping a representation of the face into rectangles using a piece-wise linear warping procedure, and dividing rectangles into a grid containing a plurality of regions.

The at least one automated processor may be further configured to select a subset of the plurality of regions that are robust to facial movements and expressions, while being sufficiently discriminant to account for changes in skin color responsive to cardiac cycle variation.

The at least one automated processor may be further configured to compute chrominance features by: for each pixel, computing a chrominance signal C as a linear combination of two signals $X_f$ and $Y_f$, such that $C = X_f - \alpha Y_f$, where $$\alpha = \frac{\sigma(X_f)}{\sigma(Y_f)}$$

and $\sigma(X_f)$, $\sigma(Y_f)$ denote the standard deviations of $X_f$, $Y_f$; band-pass filter signals the signals X and Y to obtain $X_f$, $Y_f$ respectively, where $X = 3R_n - 2G_n$, $Y = 1.5R_n + G_n - 1.5B_n$ and $R_n$, $G_n$ and $B_n$ are the normalized values of the individual color channels, wherein the color combination coefficients to derive X and Y are computed using a skin-tone standardization approach; and, for each region r=1, ..., R, compute the final chrominance features averaging the values of the chrominance signals over all the pixels.

The joint estimate may be selectively responsive to a detection of chrominance feature variations that occur within a heart-rate frequency range. The joint estimate may be selectively responsive to masked extracted regions of the face dependent on at least facial movement dependent changes. The joint estimate may be dependent on a local standard deviation over time of each extracted region of the face. The joint estimate may employ an alternating direction method of multipliers (ADMM), which solves an optimization problem by alternating a direction of the optimization while keeping other directions fixed.

The solution to the optimization problem comprises alternating the following three steps until convergence:

E/M-step: with fixed F and Z, obtaining optimal values of E and M by solving:

$$\min_E v\|E\|_* + \frac{\rho}{2}\|E - F + \rho^{-1}Z\|_\mathcal{F}^2. \quad (6)$$

$$\min_M \|M^\circ(F - C)\|_\mathcal{F}^2 - \beta\|M\|_1 + \mu\|M - \tilde{M}\|_\mathcal{F}^2 \quad (8)$$

F-step: with fixed E, Z and M, determining the optimal value of F by solving:

$$\min_F \|M^\circ(F - C)\|_\mathcal{F}^2 + \gamma Tr(FLF^T) + \frac{\rho}{2}\|F - E - \rho^{-1}Z\|_\mathcal{F}^2 \quad (11)$$

Z-step: determining value of Z:

$$Z^* = Z + \rho(E - F), \quad (14)$$

where the right-hand side represent the current values.

The at least one automated processor may be further configured to determine the largest singular value of E, which encodes the heart rate information.

DETAILED DESCRIPTION OF THE PREFERRED EMBODIMENT

Matrix Completion

Matrix completion [Goldberg2010] approaches develop from the idea that an unknown low-rank matrix can be recovered from a small set of entries. This is done by solving an optimization problem, namely, a rank minimization problem subject to some data constraints arising from the small set of entries. Matrix completion has proved successful for many computer vision tasks, when data and labels are noisy or in the case of missing data, such as multi-label image classification [Cabral2015], image retrieval and tagging [Wu2013, Chen2015], manifold correspondence finding [Kovnatsky2014], head/body pose estimation [Alameda2015] and emotion recognition from abstract paintings [Alameda2016]. Most of these works extended the original MC framework by imposing task-specific constraints. For instance, in [Chen2015] a MC problem is formulated adding a specific regularizer to address the ambiguous labeling problem. Very importantly, even if most computer-vision papers based on matrix completion are addressing classification tasks, therefore splitting the matrix to be completed between features and labels, MC techniques can be used in general, without any structural splitting. Indeed, in [Kalofolias2014] matrix completion is adopted to address the movie recommendation problem, where each column (row) represents a user (movie), and therefore each entry of the matrix shows the suitableness of a video for a user. In [Kovnatsky2014, Kalofolias2014], the MC problem is extended to take into account an underlying graph structure inducing a weighted relationship between the columns/ rows of the matrix. [Kovnatsky2014, Kalofolias2014, Alameda2015] provide certain limited predicates for modeling the temporal smoothness of the HR signal. However, the present technology is able to simultaneously recover the unknown low-rank matrix and the underlying data mask, corresponding to the most reliable observations.

HR Estimation Using SAMC

Figure 2:
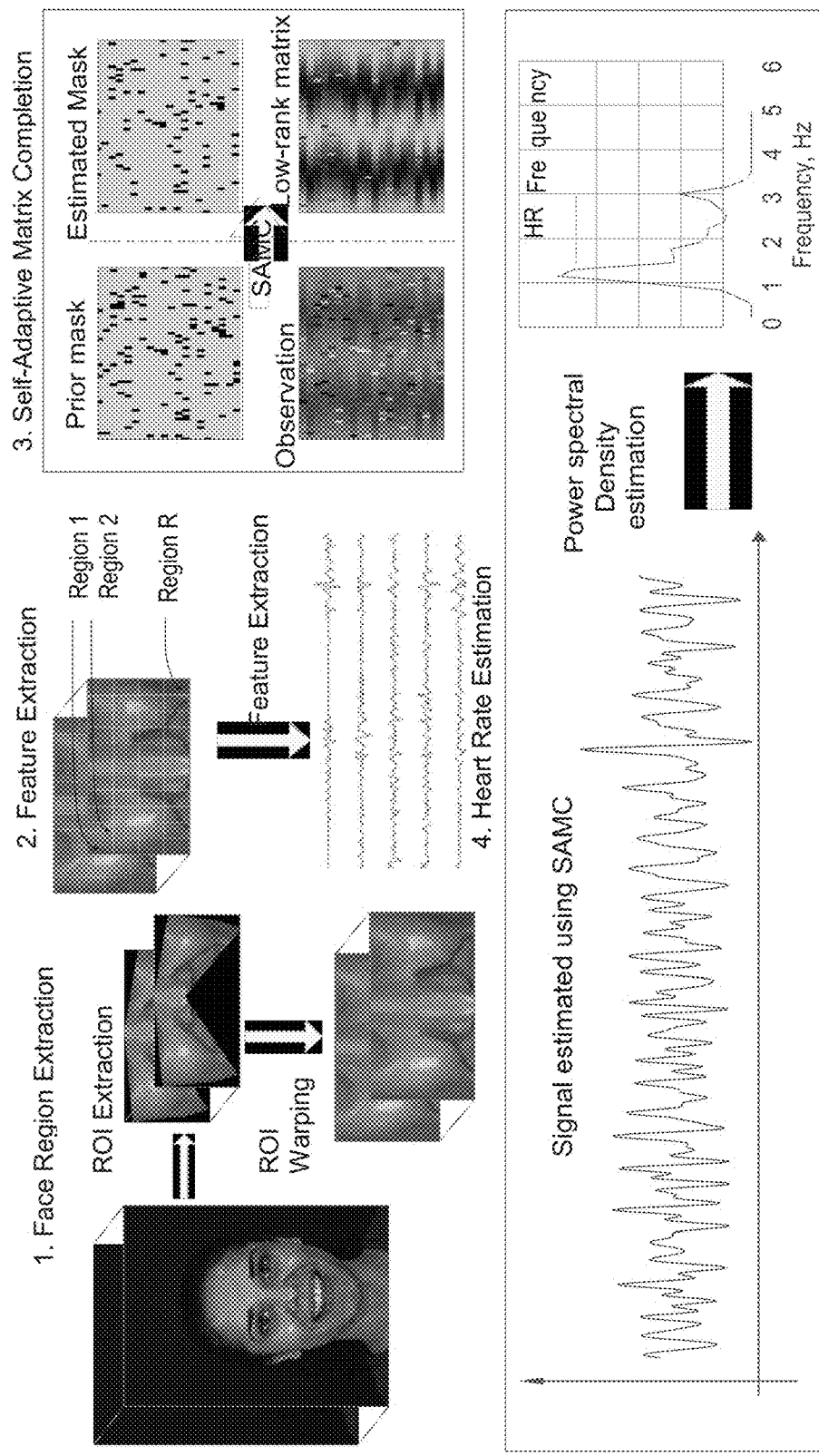
FIG. 2: Overview of the proposed approach for HR estimation. During the first phase, a set of facial keypoints is automatically detected, and then used to define a ROI. This region is then warped to a rectangular area and divided into a grid. For each small sub-region, chrominance features are computed (Phase 2). SAMC is applied on the matrix of all feature observations to recover a smooth signal, while selecting from which sub-regions the signal is recovered (Phase 3). Welch's method [Welch1967] is used to estimate the power spectral density and thus the HR frequency (Phase 4).

The proposed approach for HR estimation from face videos has four main phases as shown in FIG. 2. Phase 1 is devoted to process face images so to extract face regions, that are used in phase 2 to compute chrominance features. Phase 3 consists in the joint estimation of the underlying low-rank feature matrix and the mask using SAMC. Finally, phase 4 computes the heart rate from the signal estimate provided by SAMC.

Phases 1 & 2: From Face Videos to Chrominance Features

Intraface (www.humansensing.cs.cmu.edu/intraface) is used to localize and track 66 facial landmarks. Many approaches have been employed for face frontalization [Wang2016, Hassner2015]. However, in order to preserve the underlying blood flow signal, the facial region of interest (see FIG. 2—Phase 1) is defined from which the HR will be estimated. The potential ROI is then warped to a rectangle using a piece-wise linear warping procedure, before dividing the potential ROI into a grid containing R regions. The overall performance of the HR estimation method will strongly depend on the features extracted on each of the R sub-regions of the facial ROI. Ideally, features are selected that are robust to facial movements and expressions, while being discriminant enough to account for the subtle changes in skin color. Currently, the best features for HR estimation are the chrominance features, defined in [DeHaan2013]. The chrominance features for HR estimation are derived from the RGB channels, as follows. For each pixel the chrominance signal C is computed as the linear combination of two signals $X_f$ and $Y_f$, i.e. $C=X_f-\alpha Y_f$, where $$\alpha = \frac{\sigma(X_f)}{\sigma(Y_f)}$$

and $\sigma(X_f)$, $\sigma(Y_f)$ denote the standard deviations of $X_f$, $Y_f$. The signals $X_f$, $Y_f$ are band-passed filtered signals obtained respectively from the signals X and Y, where $X=3R_n-2G_n$, $Y=1.5R_n+G_n-1.5B_n$ and $R_n$, $G_n$ and $B_n$ are the normalized values of the individual color channels. The color combination coefficients to derive X and Y are computed using a skin-tone standardization approach (see [DeHaan2013] for details). For each region $r=1, \ldots, R$, the final chrominance features are computed averaging the values of the chrominance signals over all the pixels.

Phase 3: Self-adaptive Matrix Completion

Figure 1:
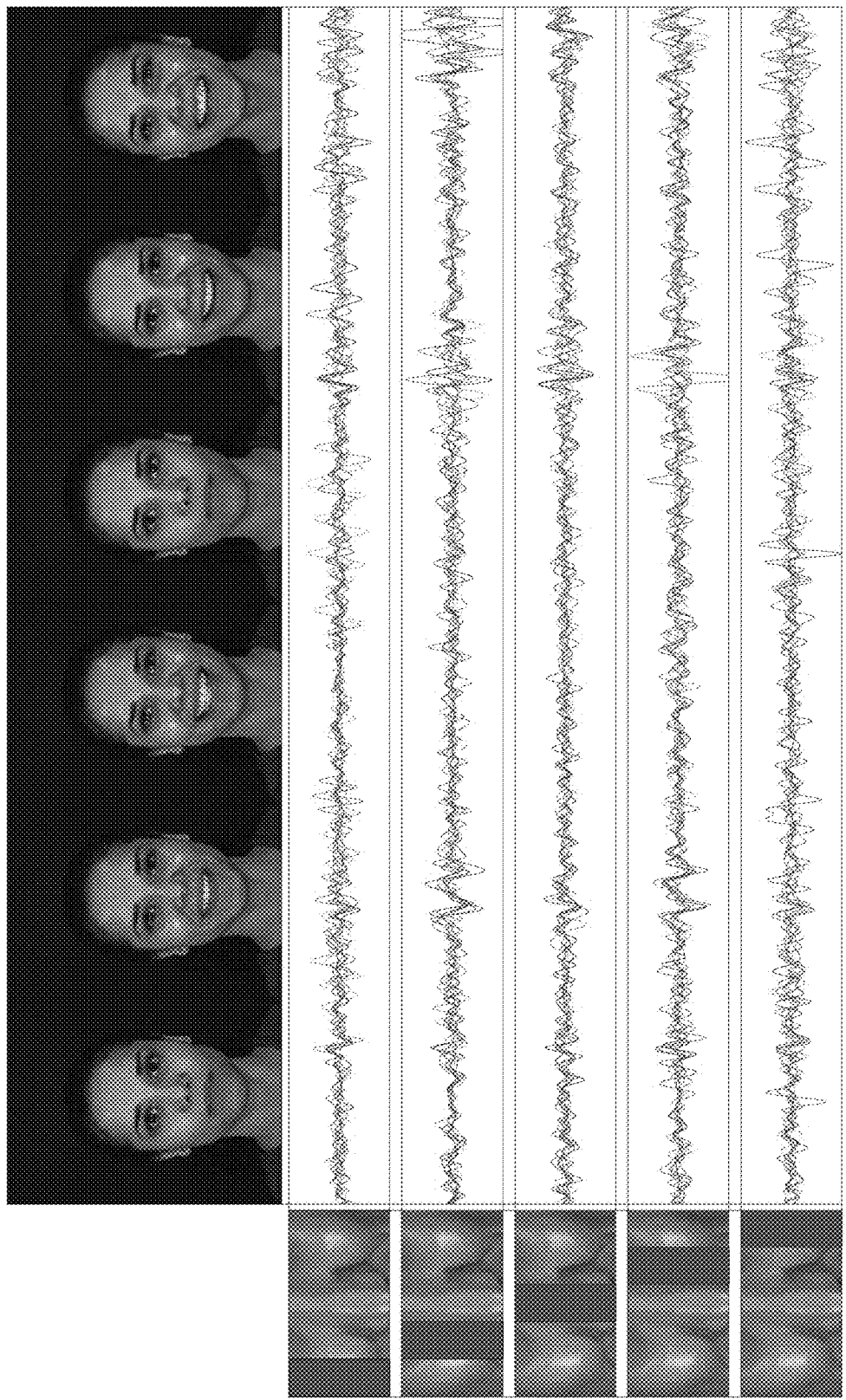
FIG. 1: Motivation: Given a video sequence, automatic HR estimation from facial features is challenging due to target motion and facial expressions. Facial features extracted over time in different parts of the face (purple rectangles) show different temporal dynamics and are subject to noise, as they are heavily affected by movements and illumination changes.

The estimation of HR from the chrominance features is challenging for mainly two reasons. Firstly, the chrominance features associated to different facial regions are not fully synchronized. In other words, even if the output signals of many regions are synchronized between them (mainstream underlying heart signal), the signal of many other regions may not be in phase with the mainstream. Secondly, face movements and facial expressions induce strong perturbations in the chrominance features. These perturbations are typically local in space and time while large in intensity (FIG. 1). Therefore, these perturbations should be localized so as not to use them in the HR estimation.

These two main difficulties are intuitively overcome by deriving a matrix completion technique embedding a self-adaptation strategy. On the one hand, since matrix completion problems are usually approached by reducing the matrix rank, the low-rank estimated matrix naturally groups the rows by their linear dependency. In this particular case, two rows are (near) linearly dependent if and only if the output signals they represent are synchronized. Therefore, the underlying HR signal is hypothesized to be in the vector subspace spanned by the largest group of linearly dependent rows of the estimated low-rank matrix.

On the other hand, the estimated low-rank matrix is enforced to resemble the observations. In previous MC approaches [Cabral2015, Chen2015, Alameda2015, Kovnatsky2014], the non-observed part of the matrix consisted of the labels of the test set. Thus, the set of unknown matrix entries was fixed and known in advance. The HR estimation problem is slightly different since there are no missing observations, i.e. the matrix is fully observed. However, many of these observations are highly noisy, thus corrupting the estimation of the HR. Importantly, it is not known in advance which are the corrupted observations. This problem naturally suggests some form of adaptation, implying that the method selects the samples with which the learning is performed. Consequently, the learning method is called self-adaptive matrix completion (SAMC).

In order to formalize the self-adaptive matrix completion problem let us assume the existence of R regions where chrominance features are computed during T video frames. This provides a chrominance observations matrix $C \in R$. Ideally, in a scenario all region features could be continuously trusted, and the low-rank matrix would simply be estimated that better approximates the matrix of observations C, by solving: $\min_E \nu \, \text{rank}(E)+\|E-C\|_F^2$, where $\nu$ is a regularization parameter. Unfortunately, minimizing the rank is a NP-hard problem, and traditionally a convex surrogate of the rank, the nuclear norm, is used [Candes2009]:

$$\min_E \nu \|E\|_* + \|E-C\|_F^2. \quad (1)$$

Another intrinsic property of the chrominance features is that, since the underlying reason of their oscillation is the internal functioning of the heart, the estimated chrominance features (those of the low-rank estimated matrix) should be enforced to be within the heart-rate's frequency range. Inspired by [Kalofolias2014, Kovnatsky2014, Alameda2015] a temporal smoothing term is added by means of a Laplacian matrix L:

$$\min_E \nu \|E\|_* + \left| \|E-C\|_F^2 + \gamma Tr(ELE^\top) \right|, \quad (2)$$

where Y measures the weight of the temporal smoothing within the learning process. L should encode the relational information between the observations acquired at different instants, thus acting like a relaxed band-pass filter. Indeed, imposing that $e_r$ is band-pass filtered is ii equivalent to reduce $\|e_r\|$, $\|e_r-e_rT\|^2=\|e_r\tilde{T}\|^2$, where each column of T is a shifted replica of the band-pass normalized filter tap values so that the product $e_rT$ boils down to a convolution and $\tilde{T}$ is a copy of T with zeros in the diagonal, since the band-pass filter is normalized. Imposing this for all R regions at once writes: $Tr(E \tilde{T}\tilde{T}^T E^T)$ and therefore $L=\tilde{T}\tilde{T}^T$.

As previously discussed, the estimated matrix should not take into account the observed entries associated to large movements or spontaneous facial expressions. This is modelled by including a masking binary matrix $M \in \{0,1\}^{R \times T}$ in the previous equation as [Cabral2015]:

$$\min_E \nu \|E\|_* + \|M \circ (E-C)\|_F^2 + \gamma Tr(ELE^\top), \quad (3)$$

where ∘ stands for the element-wise (Hadamard) product and the entries of the matrix M are 1 if the corresponding entry in C has to be taken into account for the HR estimation and 0 otherwise.

Importantly, while in the previous studies M was known in advance, according to the present application, it is estimated. This is interpreted as a form of adaptation, since M is a observation-selection variable indicating from which observations should the method learn at each iteration. The masking matrix M should select the largest possible amount of samples that provide useful information for the estimation of the HR. Moreover, when available, it would be desirable to use a prior for the mask M, taking real values between 0 and 1, $M \in [0,1]^{R \times T}$. The complete SAMC optimization problem writes:

$$\min_{E,M} \nu \|E\|_* + \|M \circ (E-C)\|_F^2 + \gamma Tr(ELE^\top) - \beta \|M\|_1 + \mu \|M-\tilde{M}\|_F^2, \quad (4)$$

The parameters $\beta$ and $\mu$ regulate respectively the number of selected observations and the importance of prior information. The prior mask $\tilde{M}$ is defined as the negative exponential of the local standard deviation of the signal. If the signal has small local standard deviation, the chrominance variation within the region is due to the heart-rate and not to head movements or facial expressions, and therefore that matrix entry should be used to estimate the HR.

Solving SAMC

The SAMC optimization problem in (4) is not jointly convex in E and M. Moreover, even in the case the masking matrix M was fixed, (4) would contain non-differential and differential terms and a direct optimization would be challenging. Instead, alternating methods have proven to be successful in solving (i) convex problems with non-differential terms and (ii) marginally convex problems that are not jointly convex. More precisely, an optimization solver is derived based on the alternating direction method of multipliers (ADMM) [Boyd2011]. In order to derive the associated ADMM method, the augmented Lagrangian problem associated to (4) is first defined:

$$\min_{E,F,M,Z} \nu\|E\|_* + \|M \circ (F-C)\|_\mathcal{F}^2 + \gamma Tr(FLF^T) - \quad (5)$$
$$\beta\|M\|_1 + \mu\|M - \tilde{M}\|_\mathcal{F}^2 + \langle Z, E-F\rangle + \frac{\rho}{2}\|E-F\|_\mathcal{F}^2,$$

where F is defined to split the terms of (5) that depend on E into those that are differential and those that are not. The variable Z represents the Lagrange multipliers constraining E to be equal to F, further regularized by the term $|E-F|_F^2$. The ADMM solves the optimization problem by alternating the direction of the optimization while keeping the other directions fixed. Specifically, solving (5) requires alternating the following three steps until convergence:

E/M-step

With fixed F and Z the optimal value of E is obtained by solving:

$$\min_E \nu\|E\|_* + \frac{\rho}{2}\|E - F + \rho^{-1}Z\|_\mathcal{F}^2. \quad (6)$$

The solution of such problem is given by the shrinkage operator applied to $F-\rho^{-1}Z$, see [Cai2010]. Formally, the singular value decomposition of $F-\rho^{-1}Z=UDV^T$, the optimal value for E, may be written as:

$$E^* = US_{\frac{\nu}{\rho}}(D)V^T, \quad (7)$$

where $S_\lambda(x)=\max(0,x-\lambda)$ is the soft-thresholding operator, applied element-wise to D in (7).

The optimal value for M is obtained from the following optimization problem:

$$\min_M \|M \circ (F-C)\|_\mathcal{F}^2 - \beta\|M\|_1 + \mu\|M - \tilde{M}\|_\mathcal{F}^2 \quad (8)$$

which can be rewritten independently for each entry of M:

$$\min_{m_{rt}\in\{0,1\}} (f_{rt} - o_{rt})^2 + m_{rt} + \mu(m_{rt} - \tilde{m}_{rt})^2 - \beta m_{rt}. \quad (9)$$

The solution is straightforward:

$$m_{rt}^* = \begin{cases} 1 & (f_{rt} - o_{rt})^2 + \mu(1 - 2m_{rt}) < \beta, \\ 0 & \text{otherwise.} \end{cases} \quad (10)$$

Intuitively, this means that a chrominance feature is selected for learning if (i) the entry of the smoothed low-rank estimation F is close to the corresponding entry in C and (ii) that chrominance feature should be selected a priori. Remarkably, this criterion is a mixture of the a posteriori representation power and the a priori knowledge.

F-step

With fixed E, Z and M, the optimal value of F is obtained by solving the following optimization problem:

$$\min_F \|M \circ (F-C)\|_\mathcal{F}^2 + \gamma Tr(FLF^T) + \frac{\rho}{2}\|F - E - \rho^{-1}Z\|_\mathcal{F}^2. \quad (11)$$

Eq. 11 is a particular case of the problem solved in [Kalofolias2014, Kovnatsky2014]. Importantly, in this case there is no need to solve a linear system of dimension RT as in [Kalofolias2014, Kovnatsky20141], R linear systems of dimension T are required to be solved, as in [Alameda2015]. From a numerical point of view this is quite advantageous, since larger linear systems tend to be numerically more unstable. More precisely, (11) can be rewritten independently for each of the R rows of F:

$$\min_{f_r} \|M_r(f_r - o_r)\|^2 + \gamma f_r L f_r^T + \frac{\rho}{2}\|f_r - e_r - \rho^{-1}z_r\|^2, \quad (12)$$

where lower-case bold letters denote rows of the respective matrices and $M_r = \text{diag}(m_r)$. The solution of the previous system is straightforward:

$$f_r^* = (2M_r + 2\gamma L + \rho I_T)^{-1}(2M_r o_r + \rho e_r + z_s), \quad (13)$$

where $I_T$ is the T-dimensional identity matrix.

Z-step

The optimal value of Z is taken from [boyd2011]:

$$Z^* = Z + \rho(E-F), \quad (14)$$

where the right-hand side represent the current values.

HR Estimation

Once the SAMC solver converges to an optimal solution for E, it can simply be hypothesized that, since the main underlying signal is the one associated to the heart rate, the largest singular value of E, would encode the information associated to the sought signal. Therefore, the singular value decomposition of E may be written as $E=UDV^T$, and it is reasonable to take the first column of V, $V_1$ as the estimated underlying HR signal. Finally, the Welch's power spectral density estimation method [Welch1967] is employed to obtain the frequency in $V_1$ with the largest energy $f_{HR}$. For the instantaneous HR measurement to get $f_{HR}$ [De-Haan2013] is followed and the highest peak in the Fourier domain of the estimated signal detected. The HR measured from the input video is then computed as $H=60 f_{HR}$.

The M2SE Database

The M2SE (MultiModal Spontaneous Emotion) dataset, contains facial videos for spontaneous emotion analysis and HR estimation. It is used herein only for HR estimation, however, it represents a useful resource for human behavior analysis. M2SE is a multimodal dataset including 2D, 3D, 4D, thermal data, and physiological data. 40 participants (17 male, 23 female) were recruited for data collection in the age range between 18 and 68 with diverse ethnic/racial ancestries, including African-American, Asian, Euro-American, Hispanic/Latino, etc. M2SE is a multimodal corpus containing spontaneous emotion data comprising of 3D dynamic model sequences, RGB videos, thermal videos, physiological data, and annotated Action Units (AUs). Thirty-four AUs were occurrence-coded by five expert FACS coders. The manually annotated AUs are 1-7, 9, 10-20, 22-24, 27-39. The intensity of five action units (6, 10, 12, 14, and 17) is coded by two expert coders.

Figure 3:
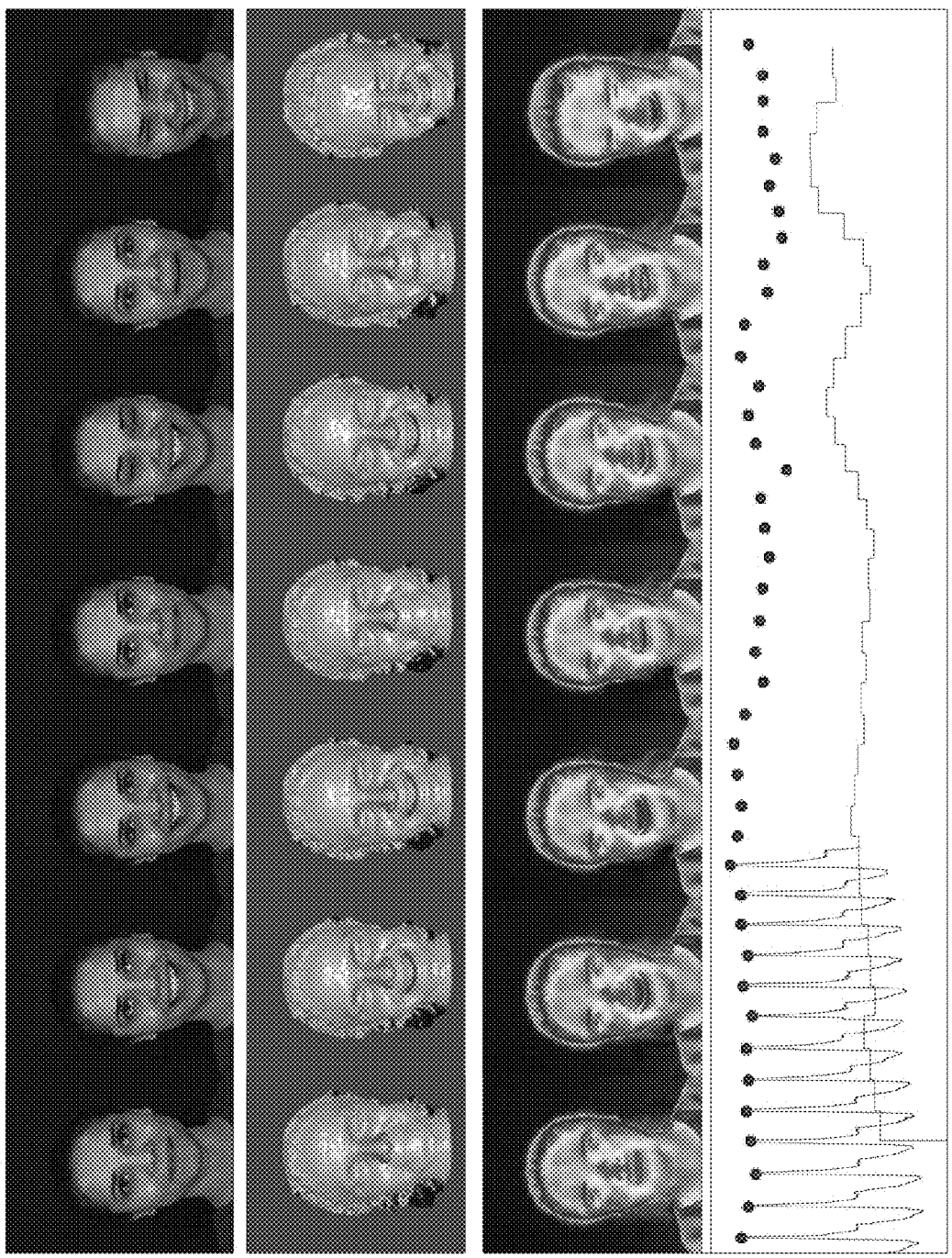
FIG. 3: Two examples of video sequences from the MMSE-HR dataset where the subjects experience fear. For each subject two rows are shown. Top: the recorded RGB-video frames. Bottom: physiological data. Note how the heart rate (the blue line) increases when each subject experiences fear.

For each subject 8 different dynamic spontaneous expression sequences were recorded. Similar to the protocol used in [Zhang2013], the emotions were elicited by a series of activities, including film watching, interviews, experiencing a cold pressor test, and other pre-designed activities. Interviews and activities elicit a wide range of authentic emotions and interpersonal behavior, including happiness/amusement, embarrassment, disgust, surprise, nervous/fear, sadness, physical pain, anger/upset, etc. Each recording lasted around 1-2 minutes. An example of a single recording is given in FIG. 3 (Note how the HR changes at the end of the sequence when the person experiences fear. This supports the value of M2SE for research on instantaneous HR estimation).

An RGB camera was used to record color videos at 25 FPS with resolution 1040×1329, while a stereo 3D camera was employed to capture geometric mesh face models with 30,000 to 50,000 vertices. The thermal camera employed was a FLIR A655sc Long-wave infrared camera, which captured thermal videos at 25 FPS with resolution 640×480, 25 Lens and 17 micron pixels with temperature range of −40 and 150 degree Celsius, and spectral range of 7.5~14.0 µm. In order to better synchronize all sensors in the system, the capture rate of the thermal sensor was set at 25 fps with the resolution of 640×480. The physiological data were collected by Biopac Mp150 data acquisition system, including heart-rate, electrocardiography and electro-dermal activity, respiration rate, systolic blood pressure, diastolic blood pressure, mean blood pressure, and EDA (skin-conductivity), working at 1 kHz. All sensors were synchronized.

Experimental Evaluation

Datasets

Experiments were conducted on two datasets: the publicly available MAHNOB-HCI dataset [Soleymani2012] and the MMSE-HR dataset. As demonstrated by the experimental results, the latter dataset contains more challenging sequences, due to subjects' movements and facial expressions.

The MAHNOB-HCI dataset is a multimodal dataset with 20 high resolution videos per subject. It contains 27 subjects (12 males and 15 females) in total, and each subject participated in two experiments: (i) emotion elicitation and (ii) implicit tagging. Following [Li2014], the experiments used a 30 second interval (frames from 306 through 2135) of 527 sequences. To compute the ground truth heart rate for each video sequence second channel (EXG2) of the corresponding ECG waveforms was used (see [Soleymani2012]).

The MMSE-HR dataset is a subset of the MMSE database [Zhang2016] specifically targeted to challenge heart rate estimation algorithms. The MMSE-HR dataset includes 102 RGB videos and heart-rate data of 40 participants with diverse ethnic/racial ancestries. Two examples are given in FIG. 3 (Note how the HR changes during the recording when each person experiences fear. This supports the value of the dataset for research on instantaneous HR estimation). The physiological data were collected by Biopac Mp150 data acquisition system (www.biopac.com), including heart-rate, mean blood pressure, and other physiological signals, working at 1 kHz. All sensors were synchronized. More details regarding data collection and recording setup can be found in [Zhang2016].

To compute the ground truth HR signal for both datasets a peak detection method from the MNE package was used (martinos.org/mne/stable/index.html).

Settings

To evaluate the performance of the proposed approach and compare it with previous methods, five commonly used metrics in the literature on remote HR analysis [Li2014] were employed. Specifically, the difference between the predicted heart rate $H_p(i)$ and the ground truth heart rate $H_{gt}(i)$ for the i-th video sequence is defined $H_e(i)=H_p(i)-H_{gt}(i)$. The mean $M_e$ and the standard deviation $SD_e$ of $H_e$ overall sequences are reported. The Root Mean Squared Error (RAISE), the mean of error-rate percentage $$M_{eRate} = \sum_{i=1}^{N} \frac{|H_e(i)|}{H_{gt}(i)}$$

and the Pearson's correlation Q between signals $H_p=\{H_p(1), \ldots, H_p(N)\}$ and $H_{gt}=\{H_{gt}(1), \ldots, H_{gt}(N)\}$, being N is the number of video sequences, is adopted. In all the herein reported experiments, the parameters of the proposed method have been selected by cross-validation on a subset of MMSE-HR and set to $v=0.0357$, $\gamma=0.01$, $\mu=0.0011$ and $\beta=0.0005$. Importantly, these parameters were used throughout all the experiments for the two datasets, supporting the generalization ability of SAMC.

Results

Average HR prediction. In the first series of experiments the present technology was compared with several state-of-the art methods for average HR prediction on the MAHNOB-HCI dataset. Specifically the approaches described in [Poh2010, Poh2011, Balakrishnan2013, Li2014, DeHaan2013] are considered. Performance on MAHNOB-HCI is given in Table 1. To perform a quantitative comparison, the methods of [Li2014] and [DeHaan2013] were implemented, since their code is not available, while the performance measures for [Poh2010, Poh2011, Balakrishnan2013] are taken from [Li2014]. A more recent method was also reimplemented based on chrominance features in [Wang2015]. It is evident that, while HR estimation on MAHNOB-HCI represents a challenging task for early methods, the more recent approaches, [Li2014] and [DeHaan2013], achieve high accuracy. Moreover, the present approach outperforms competing methods by a small margin. This can be explained by the fact that MAHNOB-HCI does not contain many sequences with subject's movements and facial expression changes, while SAMC has been designed to explicitly cope with the spatially localized and intense noise they generate.

TABLE 1

Average HR prediction: comparison among different methods on MAHNOB-HCI dataset (best performance in bold).

| Method | Me (SDe) | RMSE | MeRate | ρ |
|---|---|---|---|---|
| Poh et al. [16] | −8.95 (24.3) | 25.9 | 25.0% | 0.08 |
| Poh et al. [17] | 2.04 (13.5) | 13.6 | 13.2% | 0.36 |
| Balakrishnan et al. [3] | −14.4 (15.2) | 21.0 | 20.7% | 0.11 |
| Li et al. [15] | −3.30 (6.88) | 7.62 | 6.87% | 0.81 |
| De Haan et al. [9] | 4.62 (6.50) | 6.52 | 6.39% | 0.82 |
| SAMC | 3.19 (5.81) | 6.23 | 5.93% | 0.83 |

TABLE 2

Average HR prediction: comparison among different methods on $M^2SE$ dataset (best performance in bold).

| Method | Me (SDe) | RMSE | MeRate | ρ |
|---|---|---|---|---|
| Li et al. [15] | 11.56 (20.02) | 19.95 | 14.64% | 0.38 |
| De Haan et al. [9] | 9.41 (14.08) | 13.97 | 12.22% | 0.55 |
| SAMC | 7.61 (12.24) | 11.37 | 10.84% | 0.71 |

To demonstrate the advantages of the present method, similar experiments are performed on the more challenging sequences of the MMSE-HR dataset. Here, the method is compared against only the best-performing methods from Table 1. Table 2 reports the results of the evaluation. On this difficult dataset, due to its capacity to select the most reliable chrominance features and ignore the noisy ones, the proposed SAMC achieves significantly higher accuracy than the state-of-the-art.

TABLE 3

Short-time window analysis. Results for three windows sizes are reported: 4, 6, and 8 seconds.

| Method | Me (SDe) | RMSE | MeRate | ρ |
|---|---|---|---|---|
| 4 s De Haan et al. [9] | −1.85 (15.77) | 15.83 | 9.92% | 0.67 |
| SAMC | 2.12 (11.51) | 11.66 | 9.15% | 0.78 |
| 6 s De Haan et al. [9] | −2.21 (19.21) | 19.27 | 11.81% | 0.33 |
| SAMC | 0.32 (8.29) | 8.27 | 7.30% | 0.80 |
| 8 s De Haan et al. [9] | 0.81 (11.49) | 11.46 | 8.60% | 0.63 |
| SAMC | 1.62 (9.67) | 9.76 | 7.52% | 0.71 |

TABLE 4

Self-adapting (SA) vs. non-adapting (NA) MC.

| | p | $M_e$ ($SD_e$) | RMSE | $M_{eRate}$ | ρ |
|---|---|---|---|---|---|
| 2 * SA | 20 | 8.13 (12.08) | 12.13 | 10.74 | 0.68 |
| | 40-100 | 8.22 (12.24) | 12.23 | 10.84 | 0.67 |
| 5 * NA | 20 | 55.39 (36.86) | 65.99 | 68.21 | 0.08 |
| | 40 | 35.90 (41.29) | 51.47 | 44.76 | 0.16 |
| | 60 | 22.40 (33.79) | 37.06 | 27.91 | 0.17 |
| | 80 | 9.41 (14.53) | 14.63 | 11.91 | 0.49 |
| | 100 | 10.05 (15.23) | 15.13 | 12.98 | 0.47 |

Effect of self-adaptation. In order to show the benefits of adopting the proposed self-adaptation strategy, results with a fixed binary mask M (i.e. without self-adaptation) are provided, and compared to those obtained with self-adaptation in Table 4. The first column corresponds to the percentile of the values of the prior M used to construct the initial mask. More precisely, for a value p, the initial mask is 1 only in the entries corresponding to the p % regions with the lowest standard deviation. Therefore, p=100% corresponds to an (initial) mask matrix of all 1's. Clearly, the choice of p is crucial when the matrix is fixed, but almost irrelevant when there is self-adaptation. Also, self-adaptation systematically outperforms the fixed mask case.

Figure 4:
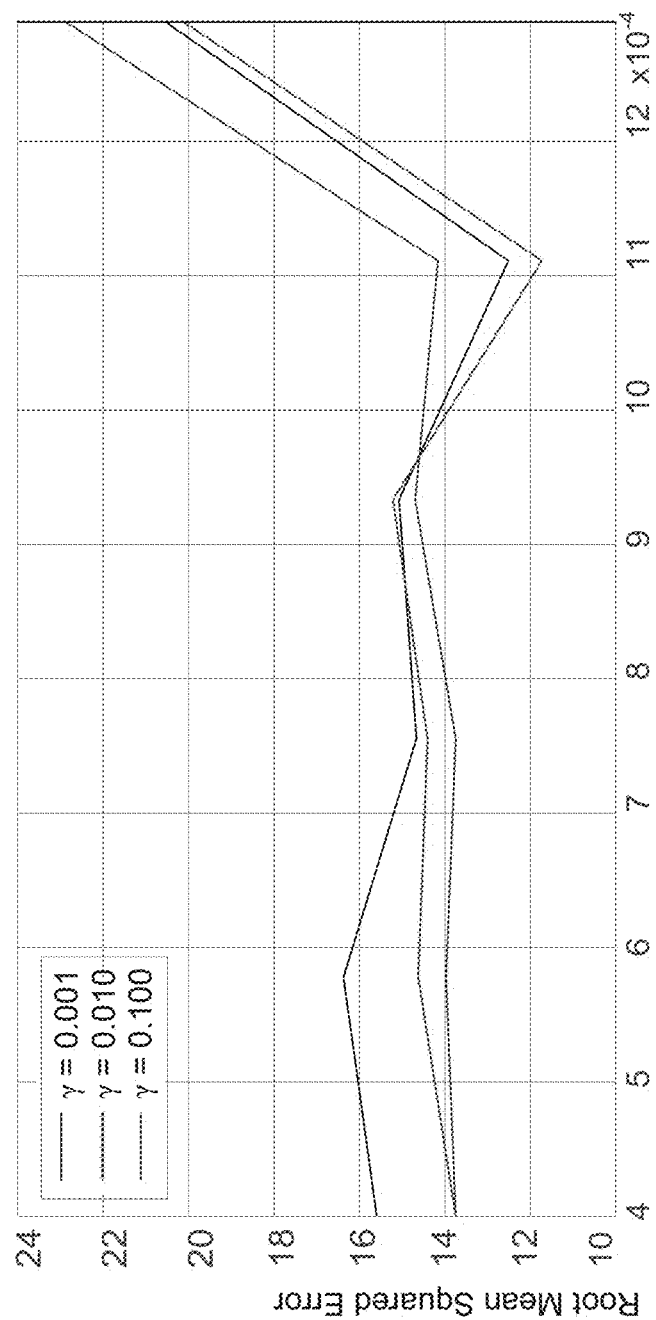
FIG. 4: Left: performance at varying values of the $\gamma$ and $\mu$. Right: RMSE dependency on $\sigma_s$.

Finally, FIG. 4 shows the performance of the proposed approach at different values of parameters μ and γ for the experiments on the M2SE dataset. As shown in the figure, very small and very large values of μ (indicating an increase and a reduction of the influence of the prior mask), correspond to a decrease of performance. Similarly, for the parameter γ, weighting the influence of the Laplacian term, a local optimum can be obtained for γ=0.01.

Effect of self-adaptation. In order to show the benefits of adopting the proposed self-adaptation strategy, results are provided with a fixed binary mask M (i.e. without self-adaptation) and compared to those obtained with self-adaptation in Table 4. The first column corresponds to the percentile of the values of the prior M used to construct the initial mask. More precisely, for a value p, the initial mask is 1 only in the entries corresponding to the p % regions with the lowest standard deviation. Therefore, p=100% corresponds to an (initial) mask matrix of all 1's. Clearly, the choice of p is crucial when the matrix is fixed, but almost irrelevant when there is self-adaptation. Also, self-adaptation systematically outperforms the fixed mask case.

Short-time HR estimation. To demonstrate the ability of the present method to recognize instantaneous HR, 20% of the recorded sequences where there is a very strong heart-rate variation were selected. Each sequence was split into non-overlapping windows of length 4, 6, and 8 seconds and process each window independently with [DeHaan2013] and SAMC, since the approach in [Li2014] is not suitable for instantaneous HR prediction. Table 3 shows the results of the short-time window analysis. The table supports the intuition that, the smaller the window, the more difficult is for a method to reliably estimate the HR. Importantly, SAMC consistently outperforms [DeHaan2013] for all window lengths and produces reliable estimates starting from the 4-second windows.

Figure 5:
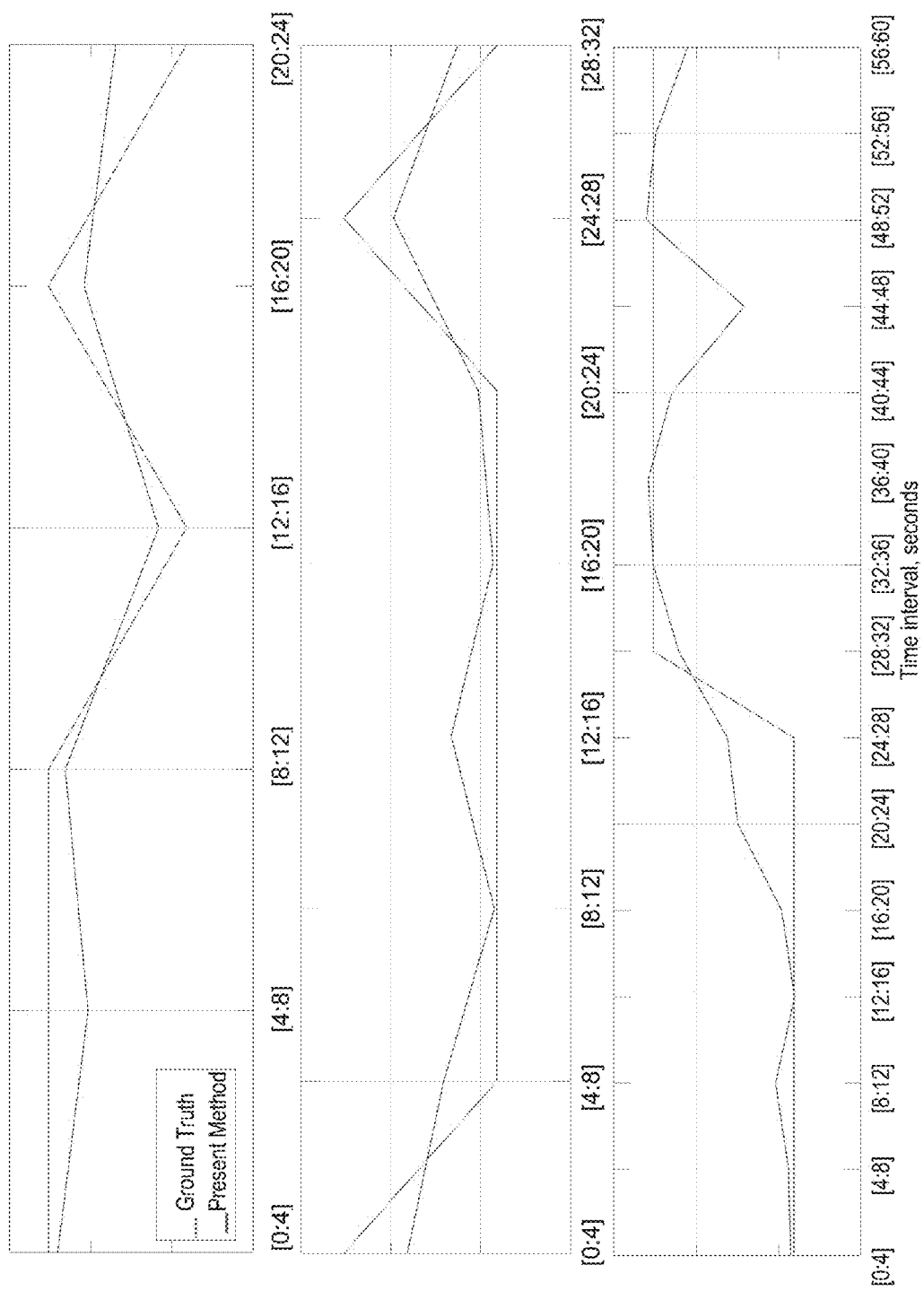
FIG. 5: Heart rate recognition results for three sequences, using window size of 4 seconds. Y-axis shows the interval over which the heart rate was computed.

To show that the present method is able to follow the changes in subject's HR, the predicted heart rate is reported for three sequences of different length. FIG. 5 shows the results of three selected video sequences processed by the present method. Note that although the method is not able to predict the exact HR for every window, providing the value close to the ground truth, a sudden increase/decrease is well localized in time.

Running time. The proposed approach is fast, enabling real-time HR analysis. On average, phase 1 runs at 50 fps, while phase 2 runs at around 30 fps. Phase 3 and 4 have the smallest execution time, reaching 550 fps. Running times were measured using a single core implementation on a conventional laptop with an Intel Core i7-4702HQ processor.

Conclusions

A framework for remote HR estimation from visual data is presented. At the core of this approach, there is an optimization framework, named self-adaptive matrix completion, which outputs the HR measurement while simultaneously selecting the most reliable face regions for robust HR estimation. This strategy permits discarding of noisy features, due to spontaneous target's movements and facial expressions. As demonstrated by experimental evaluation, the technology provides accurate HR estimates and outperforms state-of-the-art methods not only in the case of long-time windows, but also for short-time analysis. Extensive experiments conducted on the MMSE-HR dataset support the value of the adopted self-adaption strategy for HR estimation.

Environment of Operation

The present technology can be executed in an arbitrary program execution environment, or on customized processors or integrated circuits. The data processing may be local to the camera, in a remote appliance, or in the "cloud".

While only a few embodiments of the present invention have been shown and described, it will be obvious to those skilled in the art that many changes and modifications may be made thereunto without departing from the spirit and scope of the present invention as described in the following claims. All patent applications and patents, both foreign and domestic, and all other publications referenced herein are incorporated herein in their entireties to the full extent permitted by law.

The methods and systems described herein may be deployed in part or in whole through a machine that executes computer software, program codes, and/or instructions on a processor. The present invention may be implemented as a method on the machine, as a system or apparatus as part of or in relation to the machine, or as a computer program product embodied in a computer readable medium executing on one or more of the machines. The processor may be part of a server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, client, firewall, gateway, hub, router, or other such computer and/or networking hardware.

The software program may be associated with a server that may include a file server, print server, domain server, internet server, intranet server and other variants such as secondary server, host server, distributed server and the like. The server may include one or more of memories, processors, computer readable media, storage media, ports (physical and virtual), communication devices, and interfaces capable of accessing other servers, clients, machines, and devices through a wired or a wireless medium, and the like. The methods, programs, or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs, or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions described herein and elsewhere may be implemented within a wireless network, which may include cellular networks (e.g., CDMA, FDMA, TDMA, OFDM, LTE, 3GPP, 3G, 4G, 5G), local area networks (e.g., WiFi IEEE-802.11 family of protocols, Zigbee, ZWave, Bluetooth, 802.15 family of protocols, LiFi, etc.), mesh, or other networks types.

The methods, programs codes, and instructions described herein and elsewhere may be implemented on or through mobile devices. The mobile devices may include navigation devices, cell phones, smart phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer-to-peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The technology may also be implemented using security cameras, and as such may provide premises security and/or homeland security, and may further be implemented as part of a stress analyzer or "lie detector". The technology may be implemented as part of a videophone or personal feedback, or athletic training device. The technology may be employed within an interview context to determine interviewee heart rate. The technology may further be used in medical facilities to monitor patients' heart rates. Likewise, the technology may be used in retail and media environments to assess customer excitement.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

According to software or hardware engineering practices, the functions may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipments, servers, routers and the like. Furthermore, the elements depicted in the flow chart and block diagrams or any other logical component may be implemented on a machine capable of executing program instructions. Thus, while the foregoing descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application. The hardware may include a general-purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine-readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions. The technology may be implemented on single core, multiple core, RISC, CISC, SIMD, SISD, DSP, GPGPU, ASIC, CPLD, or other computational environments.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

All documents referenced herein are hereby expressly incorporated by reference in their entirety.

REFERENCES

[1] X. Alameda-Pineda, Y. Yan, E. Ricci, O. Lanz, and N. Sebe. Analyzing free-standing conversational groups: A multimodal approach. In ACM Multimedia, 2015.

[2] A. Asthana, S. Zafeiriou, S. Cheng, and M. Pantic. Robust discriminative response map fitting with constrained local models. In CVPR, 2013.

[3] G. Balakrishnan, F. Durand, and J. Guttag. Detecting pulse from head motions in video. In CVPR, 2013.

[4] S. Boyd, N. Parikh, E. Chu, B. Peleato, and J. Eckstein. Distributed optimization and statistical learning via the alternating direction method of multipliers. Foundations and Trends in Machine Learning, 3(1):1-122, 2011.

[5] R. Cabral, F. De la Torre, J. P. Costeira, and A. Bernardino. Matrix completion for weakly-supervised multi-label image classification. IEEE TPAMI, 37(1):121-135, 2015.

[6] J.-F. Cai, E. J. Cande's, and Z. Shen. A singular value thresholding algorithm for matrix completion. SIAM Journal on Optimization, 20(4):1956-1982, 2010.

[7] E. J. Cande's and B. Recht. Exact matrix completion via convex optimization. Foundations of Computational mathematics, 9(6):717-772, 2009.

[8] C.-H. Chen, V. M. Patel, and R. Chellappa. Matrix completion for resolving label ambiguity. In CVPR, 2015.

[9] G. De Haan and V. Jeanne. Robust pulse rate from chrominance-based rPPG. IEEE Transaction on Biomedical Engineering, 60(10):2878-2886, 2013.

[10] A. Goldberg, B. Recht, J. Xu, R. Nowak, and X. Zhu. Transduction with matrix completion: Three birds with one stone. In NIPS, 2010.

[11] A. Jeni, J. F. Cohn, and T. Kanade. Dense 3D Face Alignment from 2D Videos in Real-Time. In FG, 2015.

[12] A. Jourabloo and X. Liu. Pose-Invariant 3D Face Alignment. In ICCV, 2015.

[13] V. Kalofolias, X. Bresson, M. Bronstein, and P. Vandergheynst. Matrix completion on graphs. In NIPS Workshops, 2014.

[14] A. Kovnatsky, M. M. Bronstein, X. Bresson, and P. Vandergheynst. Functional correspondence by matrix completion. CVPR, 2015.

[15] X. Li, J. Chen, G. Zhao, and M. Pietikainen. Remote Heart Rate Measurement From Face Videos Under Realistic Situations. In CVPR, 2014.

[16] M.-Z. Poh, D. J. McDuff, and R. W. Picard. Non-contact, automated cardiac pulse measurements using video imaging and blind source separation. Optics express, 18(10): 10762-10774, 2010.

[17] M. Z. Poh, D. J. McDuff, and R. W. Picard. Advancements in noncontact, multiparameter physiological measurements using a webcam. IEEE Transactions on Biomedical Engineering, 58.1 (2011): 7-11.

[18] M. Soleymani, J. Lichtenauer, T. Pun, and M. Pantic. A multimodal database for affect recognition and implicit tagging. IEEE Transaction on Affective Computing, 3, 2012.

[19] S. Tulyakov and N. Sebe. Regressing a 3D face shape from a single image. In ICCV, 2015.

[20] G. Valenza, L. Citi, A. Lanata', E. P. Scilingo, and R. Barbieri. Revealing real-time emotional responses: a personalized assessment based on heartbeat dynamics. Scientific reports, 2015.

[21] W. Verkruysse, L. O. Svaasand, and J. S. Nelson. Remote plethysmographic imaging using ambient light. Optics Ex-press, 16(26):21434, 2008.

[22] W. Wang, Z. Cui, Y. Yan, J. Feng, S. Yan, X. Shu, and N. Sebe. Recurrent face aging. In CVPR, 2016.

[23] W. Wang, S. Stuijk, and G. D. Haan. Exploiting Spatial Re-dundancy of Image Sensor for Motion Robust rPPG. IEEE Transactions on Biomedical Engineering, 62(2):415-425, 2015.

[23] P. D. Welch. The use of fast fourier transform for the estimation of power spectra: A method based on time averaging over short, modified periodograms. IEEE Transactions on Audio and Electroacoustics, 15(2):70-73, 1967.

[24] H.-Y. Wu, M. Rubinstein, E. Shih, J. Guttag, F. Durand, and W. Freeman. Eulerian video magnification for revealing subtle changes in the world. In ACM Transactions on Graphics, 2012.

[25] L. Wu, R. Jin, and A. K. Jain. Tag completion for image retrieval. IEEE TPAMI, 35(3):716-727, 2013.

[26] X. Xiong and F. De La Torre. Supervised descent method and its applications to face alignment. In CVPR, 2013.

[27] S. Xu, L. Sun, and G. K. Rohde. Robust efficient estimation of heart rate pulse from video. Biomedical optics express, 5:1124-35, 2014.

[28] X. Zhang, L. Yin, J. F. Cohn, S. Canavan, M. Reale, and A. Horowitz. A high-resolution spontaneous 3D dynamic facial expression database. In FG, 2013.

[29] Z. Zhang, J. Girard, Y. Wu, X. Zhang, P. Liu, U. Ciftci, S. Canavan, M. Reale, A. Horowitz, H. Yang, J. F. Cohn, Q. Ji, and L. Yin. Multimodal spontaneous emotion corpus for human behavior analysis. In CVPR, 2016.

Akgakaya, M., Basha, T. A., Goddu. B., Goepfert, L. A., Kissinger, K. V., Tarokh, V., Manning, W. J. and Nezafat, R., 2011 Low-dimensional-structure self-learning and thresholding: Regularization beyond compressed sensing for MRI Reconstruction. Magnetic Resonance in Medicine, 66(3), pp. 756-767.

Alameda-Pineda, X., Y. Yan, E. Ricci, and N. Sebe. Recognizing emotions from abstract paintings using nonlinear matrix completion. In CVPR. 2016. 3

Allen, John. "Photoplethysmography and its application in clinical physiological measurement." Physiological measurement 28.3 (2007): R1.

Bhojanapalli, S., Sanghavi, E. S. and Ward, R., 2014. Coherent matrix completion. www.jmlr.org/proceedings/papers/v32/chenc14.pdf Bolkhovsky. Jeffrey B., Christopher G. Scully, and Ki H. Chon. "Statistical analysis of heart rate and heart rate variability monitoring through the use of smart phone cameras." 2012 Annual International Conference of the IEEE Engineering in Medicine and Biology Society. IEEE, 2012.

Bousefsaf, Frédéric, Choubeila Maaoui, and Alain Pniski. "Continuous wavelet filtering on webcam photoplethysmographic signals to remotely assess the instantaneous heart rate." Biomedical Signal Processing and Control 8.6 (2013): 568-574

Cai, J. F., Candès, E. J. and Shen, Z., 2010. A singular value thresholding algorithm for matrix completion. SIAM Journal on Optimization, 20(4), pp. 1956-1982.

Cai, T. T. and Zhou, W. X., 2016. Matrix completion via max-norm constrained optimization. Electronic Journal of Statistics, 10(1), pp. 1493-1525.

Candes, Emmanuel J., and Yaniv Plan. "Matrix completion with noise." Proceedings of the IEEE 98, no. 6 (2010): 925-936

Candes, E. J. and Plan, Y., 2011. Tight oracle inequalities for low-rank matrix recovery from a minimal number of noisy random measurements. IEEE Transactions on Information Theory. 57(4), pp. 2342-2359.

Candes, E and Romberg, J., 2007. Sparsity and incoherence in compressive sampling. Inverse problems, 23(3), p.969

Chen, Jie, et al. "RealSense=real heart rate: Illumination invariant heart rate estimation from videos." Image Processing Theory Tools and Applications (IPTA), 2016 6th International Conference on. IEEE, 2016.

Chen. Ming-Xiang. "Deep Learning on Time-Frequency Representation for Heart Rate Estimation." (2017).

Cheng, J., Ye, Q., Jiang, H., Wang, D. and Wang. C., 2013. STCDG: an efficient data gathering algorithm based on matrix completion for wireless sensor networks. IEEE Transactions on Wireless Communications. 12(2), pp. 850-861.

Cheng, J., Jiang, H., Ma, X., Liu, L., Qian, L., Tian, C. and Liu, W., 2010, December. Efficient data collection with sampling in WSNs: making use of matrix completion techniques. In Global Telecommunications Conference (GLOBECOM 2010), 2010 IEEE (pp 1-5). IEEE.

Chung, Dahjung. et al. "Improving Video-Based Heart Rate Estimation." Electronic Imaging 2016.19 (2016): 1-6.

Chwyl, Brendan, et al. "Time-frequency domain analysis via pulselets for non-contact heart rate estimation from remotely acquired photoplethysmograms." Computer and Robot Vision (CRV), 2016 13th Conference on IEEE, 2016.

Fira, M., Goras, L. and Barabasa, C., 2013, July. Reconstruction of compressed sensed ECG signals using patient specific dictionaries. In Signals, Circuits and Systems (ISSCS), 2013 International Symposium on (pp. 1-4). IEEE.

Gao, H., Lin, H., Ahn, C. B. and Nalcioglu, O., 2011 PRISM: A divide-and-conquer low-rank and sparse decomposition model for dynamic MRI. UCLA CAM Report, pp. 11-26.

Gunther, J., N Ruben and T. Moon, "Model-based (passive) heart rate estimation using remote video recording of moving human subjects illuminated by ambient light." Image Processing (ICIP). 2015 IEEE International Conference on, Quebec City, Q C, 2015, pp. 2870-2874 doi: 10.1109/ICIP.2015.7351327

Gupta, Otkrist, Dan McDuff, and Ramesh Raskar. "Real-Time Physiological Measurement and Visualization Using a Synchronized Multi-Camera System." Proceedings of the IEEE Conference on Computer Vision and Pattern Recognition Workshops. 2016.

Hamedani, Kian, Zahra Bahmani, and Amin Mohammadian. "Spatio-temporal filtering of thermal video sequences for heart rate estimation." Expert Systems with Applications 54 (2016): 88-94.

Haque, Mohammad Ahsanul, Kamal Nasrollahi, and Thomas B Moeslund. "Multimodal Estimation Of Heartbeat Peak Locations And Heartbeat Rate From Facial Video Using Empirical Mode Decomposition." Visual Analysis Of Faces With Application In Biometrics, Forensics And Health Informatics (2016): 241.

Haque, Mohammad A, Kamal Nasrollahi, and Thomas B. Moeslund. "Estimation of Heartbeat Peak Locations and Heartbeat Rate from Facial Video." Scandinavian Conference on Image Analysis. Springer, Cham, 2017.

Haque, Mohammad A., et al. "Heartbeat rate measurement from facial video." IEEE Intelligent Systems 31.3 (2016): 40-48.

Hardt, M., 2013. On the provable convergence of alternating minimization for matrix completion. arXiv preprint arxiv: 1312.0925.

Hassner, T., S. Harel, E. Paz, and R. Enbar. Effective face frontalization in unconstrained images. In CVPR, 2015. 3

Holton, Benjamin D, et al. "Signal recovery in imaging photoplethysmography." Physiological measurement 34.11 (2013): 1499.

Hu, P., Yang, S., Chen, H., Stansbury, L., Miller, C., Colton, K., Kalpakis, K., Fang, R. and Stein, D. M., 2013. Noninvasive Intracranial Pressure Monitoring Using Advanced Machine Learning Techniques (No. AFRL-SA-WP-TR-2013-0021). SCHOOL OF AEROSPACE MEDICINE WRIGHT PATTERSON AFB OH.

Hsu. YungChien, Yen-Liang Lin, and Winston Hsu. "Learning-based heart rate detection from remote photoplethysmography features." 2014 IEEE International Conference on Acoustics, Speech and Signal Processing (ICASSP). IEEE, 2014.

Hu, Y., Zhang, D., Ye, J., Li, X. and He, X., 2013. Fast and accurate matrix completion via truncated nuclear norm regularization. IEEE transactions on pattern analysis and machine intelligence, 35(9), pp. 2117-2130.

Hu. Y., Zhang, D., Liu, J., Ye, J. and He, X., 2012, August. Accelerated singular value thresholding for matrix completion In Proceedings of the 18th ACM SIGKDD international conference on Knowledge discovery and data mining (pp. 298-306). ACM.

Jain, Monika, Sujay Deb, and A. V. Subramanyam. "Face video based touchless blood pressure and heart rate estimation." Multimedia Signal Processing (MMSP), 2016 IEEE 18th International Workshop on. IEEE, 2016.

Jayadevappa, B. M, and Mallikarjun S Holi. "An Estimation Technique using FFT for Heart Rate Derived from PPG Signal." (2015).

Ji, Hui, Chaoqiang Liu, Zuowei Shen, and Yuhong Xu "Robust video denoising using low rank matrix completion." In CVPR. pp. 1791-1798. 2010.

Ji, H., Huang, S., Shen, Z. and Xu, Y., 2011. Robust video restoration by joint sparse and low rank matrix approximation. SIAM Journal on Imaging Sciences, 4(4), pp. 1122-1142.

Kamal, A. A. R., et al. "Skin photoplethysmography-a review." Computer methods and programs in biomedicine 28.4 (1989): 257-269.

Kiraly, F., Theran, L. and Tomioka, R., 2015. The algebraic combinatorial approach for low-rank matrix completion. J Mach Learn Res, 16, pp. 1391-1436.

Klopp, O., Lafond, J., Moulines, É. and Salmon, J., 2015. Adaptive multinomial matrix completion Electronic Journal of Statistics, 9(2), pp. 2950-2975.

Kranjec, Jure, et al. "Non-contact heart rate and heart rate variability measurements: A review." Biomedical Signal Processing and Control 13 (2014). 102-112.

Krishnamurthy, Akshay, and Aarti Singh. "Low-rank matrix and tensor completion via adaptive sampling." In Advances in Neural Information Processing Systems, pp. 836-844. 2013.

Kwon, Sungjun, Hyunseok Kim, and Kwang Suk Park "Validation of heart rate extraction using video imaging on a built-in camera system of a smartphone." 2012 Annual International Conference of the IEEE Engineering in Medicine and Biology Society. IEEE, 2012.

Kyal, Survi. "Constrained independent component analysis for non-obtrusive pulse rate measurements using a webcam." (2013).

Lakens, Daniel. "Using a smartphone to measure heart rate changes during relived happiness and anger." T. Affective Computing 4.2 (2013): 238-241.

Lee, Anthony, and Younghyun Kim. "Photoplethysmography as a form of biometric authentication." SENSORS, 2015 IEEE. IEEE, 2015.

Lee, C. H., Arzeno, N. M., Ho, J. C., Vikalo, H. and Ghosh, J., 2012, September. An imputation-enhanced algorithm for ICU mortality prediction. In 2012 Computing in Cardiology (pp. 253-256). IEEE.

Lee, J-S., K-W. Lin, and J-L. Syue. "Smartphone-based heart-rate measurement using facial images and a spatiotemporal alpha-trimmed mean filter." Technology and Health Care 24.s2 (2016): S777-S783.

Lempe, Georg, et al "ROI selection for remote photoplethysmography" Bildverarbeitung für die Medizin 2013. Springer Berlin Heidelberg, 2013. 99-103.

Lewandowska, Magdalena, et al. "Measuring pulse rate with a webcam—a non-contact method for evaluating cardiac activity." Computer Science and Information Systems (FedCSIS). 2011 Federated Conference on. IEEE, 2011.

Li, N. and Li, B., 2010, September. Tensor completion for on-board compression of hyperspectral images. In 2010 IEEE International Conference on Image Processing (pp. 517-520). IEEE Li, Xiaobai and Chen, Jie and Zhao, Guoying and Pietikainen, Matti, "Remote Heart Rate Measurement From Face Videos Under Realistic Situations", The IEEE Conference on Computer Vision and Pattern Recognition (CVPR), June, 2014.

Lin, Kuan-Yi, Duan-Yu Chen, and Wen-Jiin Tsai. "Face-Based Heart Rate Signal Decomposition and Evaluation Using Multiple Linear Regression." IEEE Sensors Journal 16.5 (2016): 1351-1360.

Lin, Zhouchen, Risheng Liu, and Zhixun Su. "Linearized alternating direction method with adaptive penalty for low-rank representation." In Advances in neural information processing systems, pp. 612-620. 2011.

Liu, R., Lin, Z. and Su, Z., 2013, October. Linearized alternating direction method with parallel splitting and adaptive penalty for separable convex programs in machine learning. In ACML (pp. 116-132).

Liu, Dongran, et al Heart-Rate Monitoring Using Single Camera. No. 2017-01-1434 SAE Technical Paper, 2017.

Luo, Y., Liu, T., Tao, D. and Xu, C., 2015. Multiview matrix completion for multilabel image classification. IEEE Transactions on Image Processing, 24(8), pp. 2355-2368.

Majumdar, A. and Ward, R. K., 2011. Some empirical advances in matrix completion. Signal Processing. 91(5), pp. 1334-1338.

Malacarne, Alain, et al. "Improved remote estimation of heart rate in face videos." Signal and Information Processing (GlobalSIP), 2016 IEEE Global Conference on. IEEE, 2016.

Marjanovic, G. and Solo, V, 2012. On optimization and matrix completion. IEEE Transactions on signal processing, 60(11), pp. 5714-5724.

Mascaro, Stephen A., and H. Harry Asada. "Photoplethysmograph fingernail sensors for measuring finger forces without haptic obstruction." IEEE Transactions on robotics and automation 17.5 (2001): 698-708

McDuff, Daniel, Sarah Gontarek, and Rosalind Picard. "Remote measurement of cognitive stress via heart rate variability." 2014 36th Annual International Conference of the IEEE Engineering in Medicine and Biology Society. IEEE, 2014.

McDuff, Daniel, Sarah Gontarek, and Rosalind W. Picard. "Improvements in remote cardiopulmonary measurement using a five band digital camera." IEEE Transactions on Biomedical Engineering 61.10 (2014): 2593-2601.

Melker, Richard J., Joachim S. Gravenstein, and George Worley. "Specially configured lip/cheek pulse oximeter/photoplethysmography probes. selectively with sampler for capnography, and covering sleeves for same." U.S. Pat. No. 7,127,278 24 Oct. 2006.

Mishra. B., Apuroop, K. A. and Sepulchre, R., 2012. A Riemannian geometry for low-rank matrix completion, arXiv preprint arXiv:1211.1550.

Monkaresi, Hamed, et al. "Automated detection of engagement using video-based estimation of facial expressions and heart rate." IEEE Transactions on Affective Computing 8.1 (2017): 15-28.

Ngo, T. and Saad, Y., 2012. Scaled gradients on Grassmann manifolds for matrix completion. In Advances in Neural Information Processing Systems (pp. 1412-1420).

Othman, S. B., Trad, A. and Youssef, H., 2014, August. Security architecture for at-home medical care using Wireless Sensor Network In 2014 International Wireless Communications and Mobile Computing Conference (IWCMC) (pp. 304-309). IEEE.

Poh, Ming-Zher, Daniel J. McDuff, and Rosalind W. Picard. "Non-contact, automated cardiac pulse measurements using video imaging and blind source separation." Optics express 18.10 (2010): 10762-10774.

Pursche, T., J. Krajewski, and Reinhard Moeller. "Video-based heart rate measurement from human faces." 2012 IEEE International Conference On Consumer Electronics (ICCE). IEEE, 2012.

Rapczynski, Michal, Philipp Werner, and Ayoub Al-Hamadi. "Continuous Low Latency Heart Rate Estimation from Painful Faces in Real Time." 23th International Conference on Pattern Recognition ICPR (accepted). 2016.

Recht, B. and Ré, C., 2013. Parallel stochastic gradient algorithms for large-scale matrix completion. Mathematical Programming Computation, 5(2), pp. 201-226.

Recht, B., Fazel, M. and Parrilo, P. A., 2010 Guaranteed minimum-rank solutions of linear matrix equations via nuclear norm minimization. SIAM review, 52(3), pp. 471-501.

Resit Kavsaoğlu, A. et al., "A novel feature ranking algorithm for biometric recognition with PPG signals".

Computers in Biology and Medicine, Volume 49, 1-14 (2014), dx.doi.org/10.1016/j.compbiomed.2014.03.005

Roald, Nikolai Grov. "Estimation of vital signs from ambient-light non-contact photoplethysmography." (2013).

Ruben, Nathan E Remote Heart Rate Estimation Using Consumer-Grade Cameras. Diss. Utah State University, 2015.

Schäfer, Axel, and Jan Vagedes "How accurate is pulse rate variability as an estimate of heart rate variability?: A review on studies comparing photoplethysmographic technology with an electrocardiogram." International journal of cardiology 166.1 (2013): 15-29

Scully, Christopher G., et al "Physiological parameter monitoring from optical recordings with a mobile phone." IEEE Transactions on Biomedical Engineering 59.2 (2012): 303-306.

Shelley, Kirk H. "Photoplethysmography: beyond the calculation of arterial oxygen saturation and heart rate." Anesthesia & Analgesia 105.6 (2007): S31-S36.

Sikdar, Arindam, Santosh Kumar Behera, and Debi Prosad Dogra. "Computer-Vision-Guided Human Pulse Rate Estimation: A Review." IEEE reviews in biomedical engineering 9 (2016): 91-105.

Sun, Yu, et al. "Motion-compensated noncontact imaging photoplethysmography to monitor cardiorespiratory status during exercise." Journal of biomedical optics 16.7 (2011): 077010-077010.

Takahashi, Kazuhiko, Syota Maekawa, and Masafumi Hashimoto. "Active state recognition of a person by the multimodal biological information estimated from facial image sequences." Industrial Electronics Society, IECON 2016-42nd Annual Conference of the IEEE. IEEE, 2016

Takano, Chihiro, and Yuji Ohta. "Heart rate measurement based on a time-lapse image" Medical engineering & physics 29.8 (2007): 853-857.

Tanner, J. and Wei, K., 2013. Normalized iterative hard thresholding for matrix completion. SIAM Journal on Scientific Computing, 35(5), pp. S104-S125.

Tarassenko, L, et al. "Non-contact video-based vital sign monitoring using ambient light and auto-regressive models." Physiological measurement 35.5 (2014): 807.

Tarbox, Elizabeth A., et al. "Motion correction for improved estimation of heart rate using a visual spectrum camera." SPIE Commercial+ Scientific Sensing and Imaging. International Society for Optics and Photonics, 2017.

Tasli, H. Emrah, Amogh Gudi, and Marten den Uyl. "Remote PPG based vital sign measurement using adaptive facial regions." 2014 IEEE International Conference on Image Processing (ICIP) IEEE, 2014.

Teflioudi, C., Makari, F. and Gemulla, R., 2012, December. Distributed matrix completion. In 2012 IEEE 12th International Conference on Data Mining (pp. 655-664). IEEE.

Todeschini. A., Caron, F. and Chavent, M., 2013. Probabilistic low-rank matrix completion with adaptive spectral regularization algorithms. In Advances in Neural Information Processing Systems (pp. 845-853).

Tsouri, Gill R., et al. "Constrained independent component analysis approach to nonobtrusive pulse rate measurements." Journal of biomedical optics 17.7 (2012): 0770111-0770114.

Tulyakov, Sergey, et al. "Self-adaptive matrix completion for heart rate estimation from face videos under realistic conditions." Proceedings of the IEEE Conference on Computer Vision and Pattern Recognition. 2016.

Wang, H., Zhao, R. and Cen, Y., 2014. Rank adaptive atomic decomposition for low-rank matrix completion and its application on image recovery. Neurocomputing, 145, pp. 374-380.

Wei, Lan, et al "Automatic webcam-based human heart rate measurements using laplacian eigenmap." Asian Conference on Computer Vision. Springer Berlin Heidelberg, 2012.

www.marcoaltini.com/blog/heart-rate-variability-using-the-phones-camera

Xie, K., Wang, L., Wang, X., Wen, J. and Xie, G., 2014, June. Learning from the past: intelligent on-line weather monitoring based on matrix completion. In Distributed Computing Systems (ICDCS), 2014 IEEE 34th International Conference on (pp. 176-185) IEEE.

Xu, Shuchang, Lingyun Sun, and Gustavo Kunde Rohde. "Robust efficient estimation of heart rate pulse from video." Biomedical optics express 5.4 (2014): 1124-1135.

Yadhuraj, S. R., and H. Harsha "Motion Artifact Reduction in Photoplethysmographic Signals: A Review." International Journal of Innovative Research and Development|| ISSN 2278-0211 2.3 (2013): 626-640.

Yan, M., Yang, Y. and Osher, S., 2013. Exact low-rank matrix completion from sparsely corrupted entries via adaptive outlier pursuit. Journal of Scientific Computing, 56(3), pp. 433-449.

Yan, Bryan P., et al. "Resting and Postexercise Heart Rate Detection From Fingertip and Facial Photoplethysmography Using a Smartphone Camera: A Validation Study." JMIR mHealth and uHealth 5.3 (2017).

Yang, S., Kalpakis, K., Mackenzie, C. F., Stansbury, L. G, Stein, D. M., Scalea, T. M. and Hu, P. F., 2012, December. Online recovery of missing values in vital signs data streams using low-rank matrix completion In Machine Learning and Applications (ICMLA), 2012 11th International Conference on (Vol. 1. pp. 281-287). IEEE.

Yu, Yong-Poh, et al. "Video-based heart rate measurement using short-time Fourier transform." Intelligent Signal Processing and Communications Systems (ISPACS), 2013 International Symposium on. IEEE, 2013.

Yu, Yong Poh. Dynamic heart rate estimation using facial images from video sequences/Yu Yong Poh. Diss. University of Malaya, 2016.

Zhang, Z, Z. Pi and B. Liu, "TROIKA: A General Framework for Heart Rate Monitoring Using Wrist-Type Photoplethysmographic Signals During Intensive Physical Exercise," in IEEE Transactions on Biomedical Engineering, vol. 62, no 2, pp. 522-531, Feb. 2015. doi: 10.1109/TBME.2014.2359372

Zhao. B., Haldar, J. P., Christodoulou, A. G. and Liang, Z. P., 2012. Image reconstruction from highly undersampledspace data with joint partial separability and sparsity constraints. IEEE transactions on medical imaging. 31(9), pp. 1809-1820.

sourceforge.net/projects/pulsecapture/

U.S. Pat. Nos. 4,509,528; 5,672,875; 5,810,723; 6,064,065; 6,397,093; 6,420,709; 6,491,647; 6,513,532; 6,644,976; 7,024,235; 7,127,278; 7,150,710; 7,309,315; 7,351,327; 7,625,285; 7,654,901; 7,657,292; 7,878,965; 7,887,502; 7,918,779; 8,135,448; 8,157,730; 8,180,591; 8,180,592; 8,187,201; 8,204,786; 8,206,427; 8,277,384; 8,287,434; 8,311,769; 8,311,770; 8,317,854; 8,343,026; 8,386,008; 8,437,980; 8,463,576; 8,463,577; 8,489,178; 8,542,877; 8,542,878; 8,543,185; 8,543,351; 8,548,770; 8,553,940; 8,583,402, 8,585,607; 8,606,344; 8,617,081; 8,634,591; 8,649,562, 8,666,116; 8,670,953; 8,702,607; 8,718,748; 8,725,311; 8,728,001; 8,734,360; 8,751,194; 8,755,

857; 8,768,438; 8,768,648; 8,781,791; 8,792,969; 8,801,620; 8,805,019; 8,818,041; 8,821,418; 8,838,209; 8,849,610; 8,855,384; 8,862,196; 8,868,149; 8,868,377; 8,920,332; 8,932,227; 8,935,119; 8,938,097; 8,945,017; 8,948,832; 8,954,135; 8,956,303; 8,961,185; 8,961,415; 8,961,932; 8,965,730; 8,977,347; 8,984,622; 8,998,815; 9,002,458; 9,005,129; 9,011,316; 9,014,790; 9,014,811; 9,020,185; 9,025,826; 9,036,877; 9,042,952; 9,044,149; 9,044,171; 9,053,222; 9,075,906; 9,079,060; 9,098,901; 9,113,794; 9,113,795; 9,113,823; 9,125,606; 9,149,216; 9,155,826; 9,167,991; 9,168,419; 9,198,586; 9,198,604; 9,232,915; 9,233,244; 9,237,855; 9,241,635; 9,241,674; 9,265,456; 9,282,902; 9,301,710; 9,307,917; 9,333,351; 9,336,594; 9,345,427; 9,351,649; 9,357,955; 9,364,157; 9,370,634; 9,642,536.

U.S. Pat. App. Nos: 20010049470; 20030065257; 20030068605; 20030130709; 20030195040; 20040049124; 20040072133; 20040229692; 20040230108; 20040260161; 20060009700; 20060111620; 20060253016; 20060258896; 20060293921; 20070027375; 20070073113; 20070118027; 20070207858; 20070225606; 20070225614; 20080027330; 20080045818; 20080051858; 20080067132; 20080146892; 20080190430; 20080241199; 20090143655; 20090182204; 20090203998; 20090209834; 20090226071; 20100081941; 20100217099; 20110046498; 20110082355; 20110098112; 20110098545; 20110106627; 20110112442; 20110178581; 20110251021; 20110251493; 20110270050; 20110282169; 20110311119; 20110311143; 20110319724; 20120022338; 20120053469; 20120065514; 20120078069; 20120083705; 20120083714; 20120083715; 20120083716; 20120084053; 20120084054; 20120127351; 20120141000; 20120195469; 20120195473; 20120195486; 20120197137; 20120197737; 20120203081; 20120226111; 20120226112; 20120226334; 20120226471; 20120226472; 20120253201; 20120265296; 20120308971; 20130065680; 20130073254; 20130073255; 20130079649; 20130080113; 20130096843; 20130116503; 20130131475; 20130151196; 20130158369; 20130171599; 20130197401; 20130225950; 20130268236; 20130272393; 20130276785; 20130281795; 20130281815; 20130282040; 20130283162; 20130289366; 20130294505; 20130297220; 20130310656; 20130345568; 20130345569; 20140023235; 20140023236; 20140024952; 20140028546; 20140031696; 20140037163; 20140046209; 20140051941; 20140058217; 20140067278; 20140086462; 20140094666; 20140094670; 20140104405; 20140107493; 20140114580; 20140121471; 20140125491; 20140125618; 20140125619; 20140125620; 20140127996; 20140135598; 20140135612; 20140139656; 20140148663; 20140153800; 20140155704; 20140155713; 20140155759; 20140158132; 20140180026; 20140180132; 20140192177; 20140206954; 20140206965; 20140207292; 20140213861; 20140218496; 20140221781; 20140221845; 20140221847; 20140221866; 20140228649; 20140243648; 20140253709; 20140266939; 20140273858; 20140275832; 20140275850; 20140275852; 20140275854; 20140275855; 20140275880; 20140276089; 20140276090; 20140276099; 20140276104; 20140276118; 20140276119; 20140278220; 20140278229; 20140287833; 20140288390; 20140288391; 20140288392; 20140288396; 20140288435; 20140288436; 20140288438; 20140297217; 20140297218; 20140303454; 20140305204; 20140316305; 20140323888; 20140343349; 20140343867; 20140358012; 20140358017; 20140371583; 20150005646; 20150005680; 20150005840; 20150005841; 20150011898; 20150025334; 20150025335; 20150025393; 20150025394; 20150031965; 20150051521; 20150057511; 20150080746; 20150094552; 20150101609; 20150104088; 20150105638; 20150119654; 20150119725; 20150122018; 20150125051; 20150126824; 20150126888; 20150134268; 20150141772; 20150145673; 20150148622; 20150148637; 20150148687; 20150148691; 20150164349; 20150165200; 20150173631; 20150174403; 20150182132; 20150182137; 20150186711; 20150190062; 20150190077; 20150190090; 20150192438; 20150196256; 20150196455; 20150199010; 20150201853; 20150201854; 20150208923; 20150208950; 20150216425; 20150223698; 20150223700; 20150223708; 20150229341; 20150230735; 20150236740; 20150238120; 20150241936; 20150242608; 20150245186; 20150250391; 20150257653; 20150257659; 20150259110; 20150263774; 20150264028; 20150264045; 20150265164; 20150265212; 20150272452; 20150272489; 20150272494; 20150280181; 20150280357; 20150282724; 20150282769; 20150293115; 20150293592; 20150297142; 20150309535; 20150314166; 20150317120; 20150320363; 20150351699; 20150366455; 20150366492; 20150366504; 20150366518; 20150370320; 20150374249; 20150378433; 20150379238; 20150379362; 20150379370; 20160007934; 20160008632; 20160015308; 20160022175; 20160022201; 20160022203; 20160022220; 20160023666; 20160029898; 20160029964; 20160029973; 20160036118; 20160051169; 20160055635; 20160058367; 20160058375; 20160058376; 20160062321; 20160065840; 20160066844; 20160067494; 20160074276; 20160074661; 20160084869; 20160089033; 20160094899; 20160095524; 20160095731; 20160100765; 20160100805; 20160106360; 20160106365; 20160106371; 20160110868; 20160113526; 20160113531; 20160117544; 20160117937; 20160120482; 20160143567; 20160143580; 20160148531; 20160150582; 20160150978; 20160155006; 20160157739; 20160157761; 20160166156; 20160171684; 20160191822; 20170060521; 20170060927; 20170112381; 20170112382; 20170132786.

What is claimed is:

1. A method of determining heart rate through observation of a human face, comprising:
   acquiring with at least one automated camera, a time series of images of a human face, wherein the time series of images are subject to variations between respective images of the time series in illumination and facial movements;
   adaptively selecting, with the at least one automated processor, a subset of the regions of interest of respective images of the time series of images of the human face, that exhibit a more statistically reliable heart-rate-determined variation than a non-selected subset of regions of the respective images of the human face;
   based at least on the adaptively selected subset of regions of interest of the respective images of the time series of the human face that exhibit the reliable heart-rate-determined variation, determining a heart rate, and updating the adaptively selected subset of the regions of interest that exhibit the reliable heart-rate-determined variation; and
   outputting a signal corresponding to the determined heart rate.

2. The method according to claim 1, wherein the regions of interest are selected according to at least matrix completion theory.

3. The method according to claim 1, wherein the heart rate is determined based on at least matrix completion theory.

4. The method according to claim 1, wherein the selected subset is selected dependent on at least a noise parameter of respective features of the time series of images.

5. The method according to claim 1, wherein the selected subset is selected dependent on at least a movement of the human face represented in the time series of images.

6. The method according to claim 1, wherein the selected subset is selected dependent on at least changes represented in the time series of images which represent human facial expressions.

7. The method according to claim 1, further comprising tracking the face in the time series of images to follow rigid head movements.

8. The method according to claim 1, further comprising detecting chrominance features from the time series of images comprising video images, and assessing the heart rate-determined variation based on the detected chrominance features.

9. The method according to claim 1, wherein the adaptively selected subset of the regions of interest exhibit the reliable heart-rate-determined variation through an entire period of heart rate estimation.

10. The method according to claim 1, wherein the reliable heart-rate-determined variation is a variation in chrominance.

11. The method according to claim 1, wherein the heart rate is determined in a process employing a cardiac cycle responsive filter.

12. The method according to claim 1, further comprising simultaneously recovering an unknown low-rank matrix and an underlying data mask, corresponding to most statistically reliable heart-rate-determined variation observations of the human face according to a reliability statistic.

13. A method of determining heart rate from video images, comprising:
processing, with the at least one automated processor, a stream of video images of a face from at least one automated camera, to extract a plurality of face regions;
computing chrominance features of the plurality of face regions, with at least one automated processor;
jointly estimating an underlying low-rank feature matrix and a mask of a selected subset of the plurality of face regions which have a higher statistical reliability than a non-selected subset of the plurality of face regions, using a self-adaptive matrix completion algorithm, with the at least one automated processor; and
computing the heart rate from a signal estimate provided by the self-adaptive matrix completion algorithm, with the at least one automated processor.

14. The method according to claim 13, wherein said processing comprises warping a representation of the face into rectangles using a piece-wise linear warping procedure, and dividing rectangles into a grid containing the plurality of face regions.

15. The method according to claim 14, the selected subset of the plurality of face regions being further selected to be robust to facial movements and expressions, while being sufficiently discriminant to account for changes in skin color responsive to cardiac cycle variation for said computing the heart rate.

16. The method according to claim 13, wherein said computing chrominance features comprises:
for each pixel, computing a chrominance signal C as a linear combination of two signals $X_f$ and $Y_f$ such that $C = X_f - \alpha Y_f$, where $$\alpha = \frac{\sigma(X_f)}{\sigma(Y_f)}$$

and $\sigma(X_f)$, $\sigma(Y_f)$ denote the standard deviations of $X_f$, $Y_f$;

band-pass filtering signals the signals X and Y to obtain $X_f$, $Y_f$ respectively, where $X = 3R_n - 2G_n$, $Y = 1.5R_n + G_n - 1.5B_n$ and $R_n$, $G_n$ and $B_n$ are the normalized values of the individual color channels, wherein the color combination coefficients to derive X and Y are computed using a skin-tone standardization approach;
and, for each region $r = 1, \ldots, R$, computing the final chrominance features averaging the values of the chrominance signals over all the pixels.

17. The method according to claim 13, wherein said jointly estimating comprises enforcing a detection of chrominance feature variations that occur within a heart-rate frequency range.

18. The method according to claim 13, wherein said jointly estimating comprises masking extracted regions of the plurality of face regions dependent on at least facial movement dependent changes.

19. The method according to claim 13, wherein said jointly estimating comprises determining a local standard deviation over time of each extracted region of the plurality of face regions.

20. The method according to claim 13, wherein said jointly estimating comprises employing, by the at least one automated processor, an alternating direction method of multipliers (ADMM), which solves an optimization problem by alternating a direction of the optimization while keeping other directions fixed.

21. The method according to claim 20, wherein the solving of the optimization problem comprises repetitively performing the following three steps until convergence:
E/M-step
with fixed F and Z, obtaining optimal values of E and M by solving:

$$\min_E \nu \|E\|_* + \frac{\rho}{2} \|E - F + \rho^{-1} Z\|_{\mathcal{F}}^2. \tag{6}$$

$$\min_M \|M \circ (F - C)\|_{\mathcal{F}}^2 - \beta \|M\|_1 + \mu \|M - \tilde{M}\|_{\mathcal{F}}^2 \tag{8}$$

F-step
with fixed E, Z and M, determining the optimal value of F by solving:

$$\min_F \|M \circ (F - C)\|_{\mathcal{F}}^2 + \gamma Tr(FLF^T) + \frac{\rho}{2} \|F - E - \rho^{-1} Z\|_{\mathcal{F}}^2 \tag{11}$$

Z-step
determining value of Z:

$$Z^* = Z + \rho(E - F), \tag{14}$$

where the right-hand side represent the current values.

22. The method according to claim 21, further comprising determining the largest singular value of E, which encodes the heart rate information, by the at least one automated processor.

23. A system for determining cardiac contraction timing from video images, comprising:
an input port configured to receive a time sequence of images of a human face from an automated camera;
at least one automated processor, configured to:
process the time sequence of images of the human face to extract a plurality of facial regions;
compute heartbeat-induced time-varying features of the respective plurality of facial regions;

determine a respective statistical parameter for heartbeat-induced time-varying features of the respective plurality of facial regions;

adaptively select, based on the determined respective statistical parameter, a dynamically changing subset of the plurality of facial regions having a higher statistical reliability than a non-selected subset; and compute a cardiac contraction timing based on at least the respective heartbeat-induced time-varying features of the respective selected subset of the plurality of facial regions; and an output port configured to convey a signal responsive to the cardiac contraction timing.

\* \* \* \* \*